(12) United States Patent
Blank et al.

(10) Patent No.: US 11,679,719 B2
(45) Date of Patent: *Jun. 20, 2023

(54) VEHICULAR VISION SYSTEM WITH CONSOLE VIDEO DISPLAY AND MIRROR VIDEO DISPLAY FOR EXTERIOR VIEWING CAMERAS

(71) Applicant: Magna Mirrors of America, Inc., Holland, MI (US)

(72) Inventors: Rodney K. Blank, Zeeland, MI (US); Christopher R. Koetje, Zeeland, MI (US)

(73) Assignee: Magna Mirrors of America, Inc., Holland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/649,807

(22) Filed: Feb. 3, 2022

(65) Prior Publication Data

US 2022/0153663 A1 May 19, 2022

Related U.S. Application Data

(63) Continuation of application No. 17/248,736, filed on Feb. 5, 2021, now Pat. No. 11,242,008.
(Continued)

(51) Int. Cl.
*B60R 1/08* (2006.01)
*B60R 11/02* (2006.01)
(Continued)

(52) U.S. Cl.
CPC .......... *B60R 1/081* (2013.01); *B60R 11/0235* (2013.01); *B62D 15/027* (2013.01);
(Continued)

(58) Field of Classification Search
CPC ................ B60R 1/081; B60R 11/0235; B60R 2011/0007; B60R 2300/105;
(Continued)

(56) References Cited

U.S. PATENT DOCUMENTS 2,263,382 A 11/1941 Gotzinger
2,580,014 A 12/1951 Gazda
(Continued)

*Primary Examiner* — Allen C Wong
(74) *Attorney, Agent, or Firm* — Honigman LLP

(57) ABSTRACT

A vehicular display system includes an electronic control unit (ECU) and a plurality of cameras disposed at the vehicle. The cameras capture image data and provide captured image data to the ECU. The system includes a video display screen and a video mirror display screen that are operable to display video images derived from video images provided by the ECU. When the vehicle is traveling forward at a speed below a threshold speed, the ECU generates rearward view video images derived from image data captured by a rearward viewing camera and provides the rearward view video images to the video display screen. When the vehicle is traveling forward at a speed at or above the threshold speed, the ECU generates rearward view video images derived from image data captured by a rearward viewing camera and provides the rearward view video images to the video mirror display screen.

41 Claims, 34 Drawing Sheets

Related U.S. Application Data

(60) Provisional application No. 62/706,454, filed on Aug. 18, 2020, provisional application No. 62/704,634, filed on May 19, 2020, provisional application No. 62/971,354, filed on Feb. 7, 2020.

(51) Int. Cl.
*B62D 15/02* (2006.01)
*C07C 11/21* (2006.01)
*H10K 71/13* (2023.01)
*H10K 85/10* (2023.01)
*H10K 85/60* (2023.01)
*B60R 11/00* (2006.01)
*H10K 50/15* (2023.01)
*H10K 50/16* (2023.01)
*H10K 50/18* (2023.01)
*H10K 50/17* (2023.01)

(52) U.S. Cl.
CPC ............ *C07C 11/21* (2013.01); *H10K 71/135* (2023.02); *H10K 85/141* (2023.02); *H10K 85/615* (2023.02); *H10K 85/631* (2023.02); *B60R 2011/0007* (2013.01); *B60R 2300/105* (2013.01); *B60R 2300/607* (2013.01); *B60R 2300/806* (2013.01); *B60R 2300/8026* (2013.01); *B60R 2300/8046* (2013.01); *H10K 50/15* (2023.02); *H10K 50/16* (2023.02); *H10K 50/171* (2023.02); *H10K 50/18* (2023.02)

(58) Field of Classification Search
CPC ...... B60R 2300/607; B60R 2300/8026; B60R 2300/8046; B60R 2300/806; H10K 71/135; H10K 85/631; H10K 85/615; H10K 85/141; H10K 50/16; H10K 50/18; H10K 50/171; H10K 50/15; B62D 15/027; C07C 11/21
USPC .......................................................... 257/40
See application file for complete search history.

(56) References Cited

U.S. PATENT DOCUMENTS

| | | |
|---|---|---|
| 3,266,016 A | 8/1966 | Maru |
| 4,499,451 A | 2/1985 | Suzuki et al. |
| 4,588,267 A | 5/1986 | Pastore |
| 4,623,222 A | 11/1986 | Itoh et al. |
| 4,630,904 A | 12/1986 | Pastore |
| 4,721,364 A | 1/1988 | Itoh et al. |
| 4,906,085 A | 3/1990 | Sugihara et al. |
| 5,313,335 A | 5/1994 | Gray et al. |
| 5,355,284 A | 10/1994 | Roberts |
| 5,436,741 A | 7/1995 | Crandall |
| 5,481,409 A | 1/1996 | Roberts |
| 5,530,240 A | 6/1996 | Larson et al. |
| 5,550,677 A | 8/1996 | Schofield et al. |
| 5,575,552 A | 11/1996 | Faloon et al. |
| 5,587,699 A | 12/1996 | Faloon et al. |
| 5,668,663 A | 9/1997 | Varaprasad et al. |
| 5,670,935 A | 9/1997 | Schofield et al. |
| 5,724,187 A | 3/1998 | Varaprasad et al. |
| 5,760,962 A | 6/1998 | Schofield et al. |
| 5,786,772 A | 7/1998 | Schofield et al. |
| 5,788,357 A | 8/1998 | Muth et al. |
| 5,796,094 A | 8/1998 | Schofield et al. |
| 5,938,320 A | 8/1999 | Crandall |
| 6,005,724 A | 12/1999 | Todd |
| 6,045,243 A | 4/2000 | Muth et al. |
| 6,097,023 A | 8/2000 | Schofield et al. |
| 6,111,683 A | 8/2000 | Cammenga et al. |
| 6,257,746 B1 | 7/2001 | Todd et al. |
| 6,264,353 B1 | 7/2001 | Caraher et al. |
| 6,329,925 B1 | 12/2001 | Skiver et al. |
| 6,356,376 B1 | 3/2002 | Tonar et al. |
| 6,396,397 B1 | 5/2002 | Bos et al. |
| 6,512,624 B2 | 1/2003 | Tonar et al. |
| 6,690,268 B2 | 2/2004 | Schofield et al. |
| 6,700,692 B2 | 3/2004 | Tonar et al. |
| 7,184,190 B2 | 2/2007 | McCabe et al. |
| 7,195,381 B2 | 3/2007 | Lynam et al. |
| 7,255,451 B2 | 8/2007 | McCabe et al. |
| 7,274,501 B2 | 9/2007 | McCabe et al. |
| 7,338,177 B2 | 3/2008 | Lynam |
| 7,370,983 B2 | 5/2008 | DeWind et al. |
| 7,446,650 B2 | 11/2008 | Scholfield et al. |
| 7,446,924 B2 | 11/2008 | Schofield et al. |
| 7,492,281 B2 | 2/2009 | Lynam et al. |
| 7,581,859 B2 | 9/2009 | Lynam |
| 7,626,749 B2 | 12/2009 | Baur et al. |
| 7,688,221 B2 | 3/2010 | Watanabe et al. |
| 7,777,611 B2 | 8/2010 | Desai |
| 7,855,755 B2 | 12/2010 | Weller et al. |
| 7,965,336 B2 | 6/2011 | Bingle et al. |
| 9,041,806 B2 | 5/2015 | Baur et al. |
| 9,085,261 B2 | 7/2015 | Lu et al. |
| 9,126,525 B2 | 9/2015 | Lynam et al. |
| 9,264,672 B2 | 2/2016 | Lynam |
| 9,446,713 B2 | 9/2016 | Lu et al. |
| 9,609,757 B2 | 3/2017 | Steigerwald |
| 9,762,880 B2 | 9/2017 | Pflug |
| 9,900,490 B2 | 2/2018 | Ihlenburg et al. |
| 9,900,522 B2 | 2/2018 | Lu |
| 10,046,706 B2 | 8/2018 | Larson et al. |
| 10,071,687 B2 | 9/2018 | Ihlenburg et al. |
| 10,166,924 B2 | 1/2019 | Baur |
| 10,264,219 B2 | 4/2019 | Mleczko et al. |
| 10,300,856 B2 | 5/2019 | Baur et al. |
| 10,421,404 B2 | 9/2019 | Larson et al. |
| 10,442,360 B2 | 10/2019 | LaCross et al. |
| 11,242,008 B2 | 2/2022 | Blank et al. |
| 2005/0187675 A1 | 8/2005 | Schofield et al. |
| 2006/0050018 A1 | 3/2006 | Hutzel et al. |
| 2009/0040306 A1 | 2/2009 | Foote et al. |
| 2012/0162427 A1 | 6/2012 | Lynam |
| 2012/0236152 A1 | 9/2012 | De Wind et al. |
| 2014/0085472 A1 | 3/2014 | Lu et al. |
| 2014/0098230 A1 | 4/2014 | Baur |
| 2014/0160276 A1 | 6/2014 | Pliefke et al. |
| 2014/0244111 A1 | 8/2014 | Gross et al. |
| 2014/0285666 A1 | 9/2014 | O'Connell et al. |
| 2015/0002670 A1 | 1/2015 | Bajpai |
| 2015/0022664 A1 | 1/2015 | Pflug et al. |
| 2015/0217693 A1 | 8/2015 | Pliefke et al. |
| 2016/0337594 A1 | 11/2016 | Morishita et al. |
| 2017/0050672 A1 | 2/2017 | Gieseke et al. |
| 2017/0217372 A1 | 8/2017 | Lu et al. |
| 2017/0232890 A1 | 8/2017 | Lewis et al. |
| 2017/0254873 A1 | 9/2017 | Koravadi |
| 2017/0302889 A1 | 10/2017 | Koravadi |
| 2017/0355312 A1 | 12/2017 | Habibi et al. |
| 2018/0134217 A1 | 5/2018 | Peterson et al. |
| 2018/0215382 A1 | 8/2018 | Gupta et al. |
| 2018/0253608 A1 | 9/2018 | Diessner et al. |
| 2018/0276838 A1 | 9/2018 | Gupta et al. |
| 2018/0276839 A1 | 9/2018 | Diessner et al. |
| 2018/0276908 A1 | 9/2018 | Mader et al. |
| 2019/0016264 A1 | 1/2019 | Potnis et al. |
| 2019/0039649 A1 | 2/2019 | Gieseke et al. |
| 2019/0042864 A1 | 2/2019 | Pliefke et al. |
| 2019/0047475 A1 | 2/2019 | Uken et al. |
| 2019/0061628 A1 | 2/2019 | Kanagaraj et al. |
| 2019/0064831 A1 | 2/2019 | Gali et al. |
| 2019/0118717 A1 | 4/2019 | Blank et al. |
| 2019/0118860 A1 | 4/2019 | Gali et al. |
| 2019/0143895 A1 | 5/2019 | Pliefke et al. |
| 2019/0146297 A1 | 5/2019 | Lynam et al. |
| 2019/0258131 A9 | 8/2019 | Lynam et al. |
| 2019/0297233 A1 | 9/2019 | Gali et al. |
| 2019/0327415 A1* | 10/2019 | Prabhakar .............. H04N 23/63 |
| 2019/0347825 A1 | 11/2019 | Gupta et al. |

(56) References Cited

U.S. PATENT DOCUMENTS

| | | |
|---|---|---|
| 2020/0017143 A1 | 1/2020 | Gali |
| 2020/0042805 A1 | 2/2020 | Satomi et al. |
| 2020/0156543 A1 | 5/2020 | Kubota et al. |
| 2020/0377022 A1 | 12/2020 | LaCross et al. |
| 2021/0094473 A1 | 4/2021 | Gali et al. |
| 2021/0107465 A1* | 4/2021 | Hiei .................... G06V 20/586 |
| 2021/0114657 A1 | 4/2021 | Lu et al. |
| 2021/0155167 A1 | 5/2021 | Lynam et al. |
| 2021/0162926 A1 | 6/2021 | Lu |
| 2021/0213791 A1* | 7/2021 | Ionascu .................. G01S 15/86 |
| 2021/0300247 A1 | 9/2021 | Inaba et al. |

* cited by examiner

3. Display and PCBA To Chassis

2. Place Frame On EC Cell

1. Touch Assembly with Customer Branding On EC Cell

5. Housing and Rain Sensor Closeout and Final Function Test

4. Bracket Assembly to Chassis

- (27.0 x 27.0)mm Front Cover
- (28.6 x 28.6)mm Back Cover
- (23 x 23)mm Single PCBA
- Rosenberger Fakra Insert
- Lens Alignment
- 50° Lens
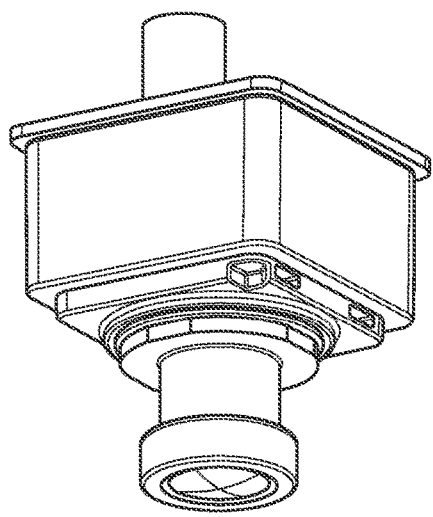
FIG. 23
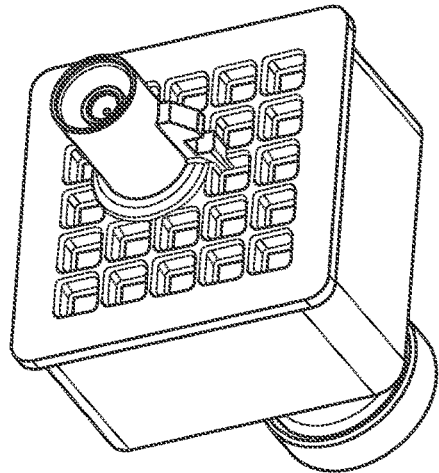
FIG. 24
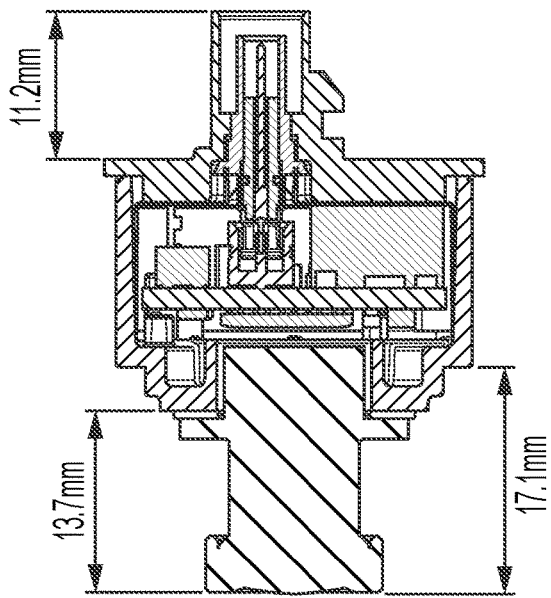
FIG. 26
FIG. 25

VEHICULAR VISION SYSTEM WITH CONSOLE VIDEO DISPLAY AND MIRROR VIDEO DISPLAY FOR EXTERIOR VIEWING CAMERAS

CROSS REFERENCE TO RELATED APPLICATIONS

The present application is a continuation of U.S. patent application Ser. No. 17/248,736, filed Feb. 5, 2021, now U.S. Pat. No. 11,242,008, which claims the filing benefits of U.S. provisional application Ser. No. 62/706,454, filed Aug. 18, 2020, U.S. provisional application Ser. No. 62/704,634, filed May 19, 2020, and U.S. provisional application Ser. No. 62/971,354, filed Feb. 7, 2020, which are all hereby incorporated herein by reference in their entireties.

FIELD OF THE INVENTION

The present invention relates to vehicular vision systems that display video images derived from image data captured by one or more cameras of the vehicle.

BACKGROUND OF THE INVENTION

It is known to provide a video display at the exterior rearview mirror assembly, such as described in U.S. Pat. No. 7,777,611, which is hereby incorporated herein by reference in its entirety, or to provide a video display at an interior rearview mirror assembly to display sideward and/or rearward images, such as described in U.S. Pat. No. 5,670,935, which is hereby incorporated herein by reference in its entirety. A variety of interior and exterior mirror assemblies with indicators are known in the art, such as U.S. Pat. Nos. 5,668,663; 5,355,284; 5,788,357; 6,257,746; 6,005,724; 5,481,409; 6,111,683; 6,045,243; 6,264,353; 6,512,624; 6,356,376; 2,263,382; 2,580,014; 3,266,016; 4,499,451; 4,588,267; 4,630,904; 4,623,222; 4,721,364; 4,906,085; 5,313,335; 5,587,699; 5,575,552; 5,436,741; 5,587,699; 5,938,320; 6,700,692 and 5,786,772, which are all hereby incorporated herein by reference in their entireties.

SUMMARY OF THE INVENTION

The present invention provides a vehicular vision system that displays video images at a video display screen of an interior rearview mirror assembly for a camera monitoring system, a rear backup camera system, and a surround view vision system, while also or selectively displaying video images at a center console or stack video display screen (such as at a center console or elsewhere at the instrument panel or dashboard of the vehicle, such as at the instrument cluster in front of the driver of the vehicle) for the rear backup camera system and the surround view vision system. The system includes an electronic control unit (ECU) of the vehicle that receives image data captured by the rear backup camera, surround view vision cameras (such as a front forward viewing camera, a driver-side sideward viewing camera, a passenger-side sideward viewing camera and the rear backup camera) and the camera monitoring system cameras (such as a rearward viewing camera, a driver-side rearward viewing camera and a passenger-side rearward viewing camera), and outputs (such as via a respective coaxial cable) to the video display of the interior rearview mirror assembly and the video display of the center console for displaying video images at the respective display screen based on the driving situation and/or user input by the driver.

The processing of image data captured by all of the cameras (optionally including a trailer camera disposed at a trailer that is being towed by the vehicle) is performed by a data processor or image processor at the ECU, such that less processing capabilities are needed at the video display devices at the interior rearview mirror assembly and at the center console. The ECU may automatically adjust the outputs to the display devices based on the driving conditions so the appropriate video images are displayed by one or more display devices for viewing by the driver of the vehicle.

For example, during normal forward driving conditions along a road, the interior mirror may be operated for displaying rearward images captured by the rearward viewing camera and/or for displaying CMS (Camera Monitoring System) images captured by the rearward viewing camera, the driver-side rearward viewing camera and the passenger-side rearward viewing camera. When the vehicle is reversing or parking, surround view video images (and rear backup camera video images) may be displayed at the video display of the center console and optionally rear backup camera video images may be displayed at the video display of the interior rearview mirror. The switch from displaying (at the video mirror display) rear backup camera video images to displaying CMS video images may be responsive to the speed of the vehicle, as the vehicle speeds up, such as following completion of an unparking maneuver (where the vehicle pulls out of a parking space and begins driving along a road).

Optionally, the system may include a trailer camera and the processor at the ECU may process image data captured by the trailer camera and may display trailer see-through images, which shows a rearward and transparent view through the trailer with seamless stitching of images and image data captured by the towing vehicle's rear backup camera with images and image data captured by the trailer camera to provide the rearward video images. The ECU may output the trailer see-through images to the video display of the center stack or console when the vehicle is traveling forward at slow speeds (such as less than 15 mph or less than 10 mph or less than 7 mph or the like), and may automatically switch to output the trailer see-through images to the video display of the interior rearview mirror when the vehicle speeds up and is traveling forward at higher speeds (such as greater than 15 mph or greater than 10 mph or greater than 7 mph or the like). Thus, when the vehicle is traveling slowly, the driver may view the trailer see-through images at the larger center console display screen, and when the vehicle is traveling at greater speeds, the driver can view the trailer see-through images at the interior mirror display so that the images can be viewed without the driver having to take his or her eyes off the road ahead of the vehicle.

These and other objects, advantages, purposes and features of the present invention will become apparent upon review of the following specification in conjunction with the drawings.

BRIEF DESCRIPTION OF THE DRAWINGS

FIGS. 23-25 are views of the camera of FIG. 22;

FIG. 26 is a sectional view of the camera of FIG. 22;

DESCRIPTION OF THE PREFERRED EMBODIMENTS

A vehicle vision system and/or driver or driving assist system and/or object detection system and/or alert system operates to capture images exterior of the vehicle and may process the captured image data to display images and to detect objects at or near the vehicle and in the predicted path of the vehicle, such as to assist a driver of the vehicle in maneuvering the vehicle in a rearward direction. The vision system includes an image processor or image processing system that is operable to receive image data from one or more cameras and to provide an output to one or more display devices for displaying video images representative of the captured image data. For example, the vision system may provide a rearview display or a top down or bird's eye or surround view display or the like.

Figure 1:
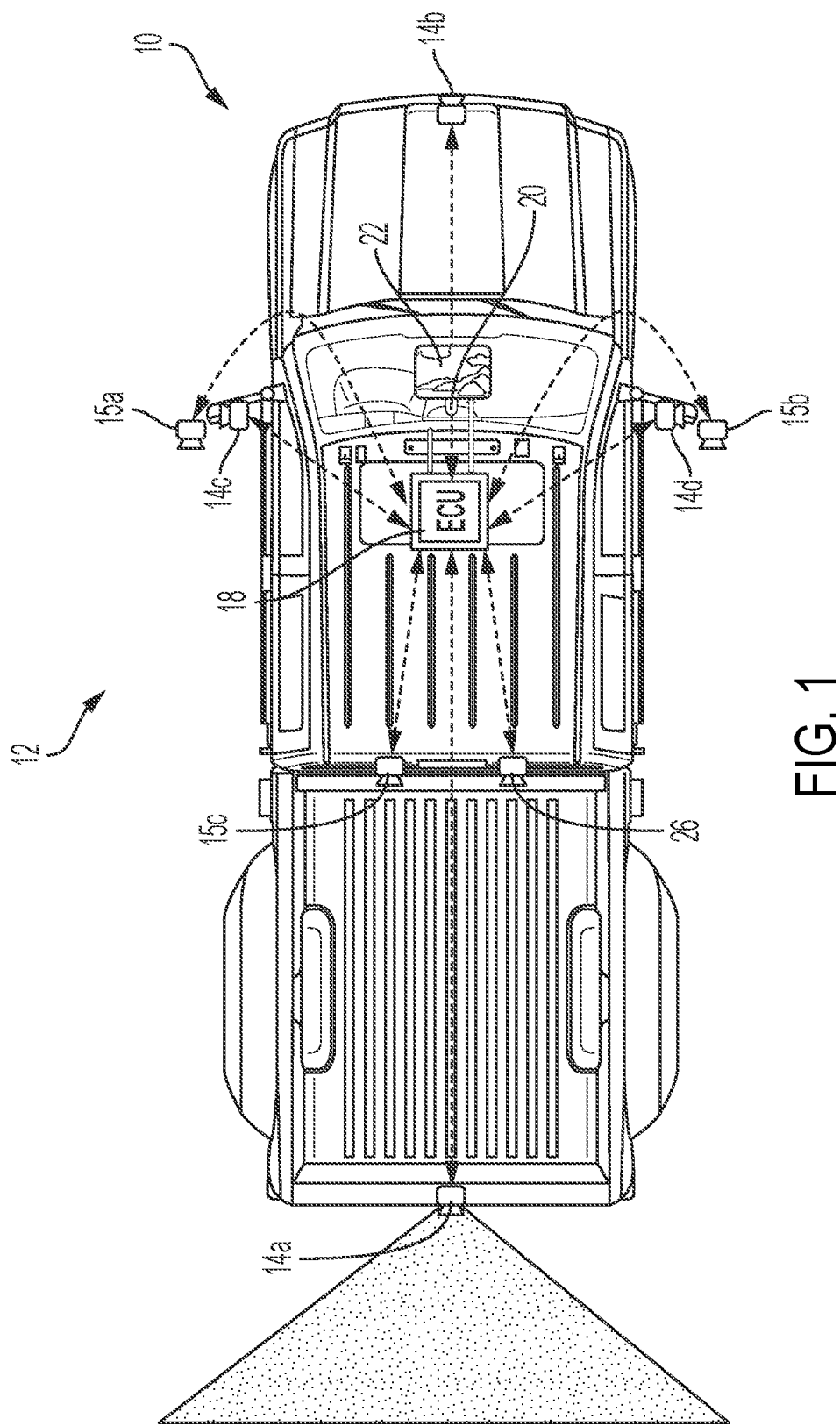
FIG. 1 is a plan view of a vehicle having a vision system in accordance with the present invention.

Referring now to the drawings and the illustrative embodiments depicted therein, a vehicle 10 includes an imaging system or vision system 12 that includes multiple exterior viewing cameras, including, for example, surround view cameras 14a-d (including a rearward viewing or rear backup camera 14a, a forward viewing camera 14b at the front of the vehicle and side surround view cameras 14c, 14d at respective sides of the vehicle), camera monitoring system (CMS) cameras 15a-c (including side rearward viewing CMS cameras 15a, 15b at the respective sides of the vehicle, and a rearward viewing camera 15c that has a different field of view than the rear backup camera 14a), which capture image data of the respective scenes exterior of the vehicle and in the field of view of the respective camera, with each camera having a lens for focusing images at or onto an imaging array or imaging plane or imager of the camera (FIG. 1). Optionally, a forward viewing camera 16 (FIG. 3) may be disposed at the windshield of the vehicle and view through the windshield and forward of the vehicle, such as for a machine vision system (such as for traffic sign recognition, headlamp control, pedestrian detection, collision avoidance, lane marker detection and/or the like). The system may utilize aspects of the systems described in U.S. Pat. Nos. 10,442,360; 10,421,404; 10,166,924 and/or 10,046,706, and/or U.S. Publication Nos. US-2019-0258131; US-2019-0047475; US-2019-0118717 and/or US-2017-0355312, which are all hereby incorporated herein by reference in their entireties.

The vision system 12 includes a control or electronic control unit (ECU) 18 having electronic circuitry and associated software, with the electronic circuitry including a data processor or image processor that is operable to process image data captured by the cameras, whereby the ECU may detect or determine presence of objects or the like and/or the system may provide video images to a display device of the interior rearview mirror assembly 20 of the vehicle for viewing by the driver of the vehicle and/or to a display device 22 at the center console or stack (such as at a center console or elsewhere at the instrument panel or dashboard of the vehicle, such as at the instrument cluster in front of the driver of the vehicle) of the vehicle (and optionally to CMS displays at or near the driver and passenger side A-pillars of the vehicle, such as described in U.S. Publication Nos. US-2018-0134217 and/or US-2014-0285666, which are hereby incorporated herein by reference in their entireties). The data transfer or signal communication from the cameras to the ECU may comprise any suitable data or communication link, such as via Texas Instrument's FPD-LINK III, or Maxim Integrated's GMSL2, low voltage differential signaling (LVDS), or ethernet, or such as a vehicle network bus or CAN (Controller Area Network) bus or LIN (Local Interconnect Network) bus or I2C bus or the like of the equipped vehicle.

The ECU receives image data captured by each of the cameras and the image data is processed by the data processor or image processor of the ECU. The ECU is connected to the video display of the mirror assembly 20 via a single coaxial wire or cable for communicating with the display (such as to provide control signals or the like) and for providing video image signals to the display. The ECU is also connected to the video display 22 of the center console via a single coaxial wire or cable for communicating with the display and for providing video image signals to the display. Thus, the ECU can provide video images to the center stack display or head unit 22 and/or to the video mirror display 20 via a dual output, with each of the dual outputs providing video image signals to the respective display over a respective coaxial cable.

As will be described further below, the ECU may be operable to provide the same or different video image signals to each of the center console video display 22 and video mirror display 20 via their respective coaxial cables. In cases where the ECU provides different video image signals to each of the center console video display 22 and video mirror display 20, the different video image signals may be derived from different portions of the same set of captured image data or derived from different sets of captured image data. For example, the ECU may simultaneously communicate video image signals representative of an upper portion of the rearward field of view of one or both of the rearward viewing cameras 14a, 15c to the video mirror display 20 and communicate video image signals representative of a lower portion of the same rearward field of view to the center console display 22 (views representative of different portions of the same set of captured image data at each display). Or, for example, the ECU may simultaneously communicate video image signals representative of a rearward field of view of one or both of the rearward viewing cameras 14a, 15c to the video mirror display 20 and communicate video image signals representative of a sideward field of view of one or more of the side-viewing surround view cameras 14c, 14d or of the side-viewing CMS cameras 15a, 15b (such as for a blind spot monitoring system) at the center console display 22 (views representative of different sets of captured image data at each display). Thus, the ECU may be operable to communicate video image signals representative of the same set of captured image data, different portions of the same set of captured image data, and/or different sets of captured image data to the different displays with which it communicates for displaying the same or different video images at the two displays. The display of different video images may be selectable and/or changeable responsive to a user input, a driving condition of the vehicle, and/or an orientation of one or more display screens in the vehicle (such as an orientation of the video mirror display screen when the interior mirror is adjusted by the driver of the vehicle).

The ECU may be limited or restricted as to what video images are provided to the center console display depending on speed or travel of the vehicle to be in compliance with Federal Motor Vehicle Safety Standard (FMVSS) 111—Rear Visibility (which is hereby incorporated herein by reference in its entirety). For example, following a reversing maneuver (during which video images derived from image data captured by the rear backup camera and optionally surround view images derived from image data captured by the surround view cameras), and after the vehicle is shifted into a forward gear, display of rearview video images (derived from image data captured by the rear backup camera) shall not be available at the end of the reversing maneuver, which may be defined by the vehicle traveling forward at a speed of 10 mph, the vehicle traveling forward a distance of 10 meters, or the vehicle traveling forward for a continuous duration of 10 seconds. The ECU may still provide selected or appropriate CMS camera views to either display screen, but may be limited as to the surround view images that may be provided when the vehicle is traveling forward.

The connections between the cameras and the ECU and/or between the displays and the ECUs may be made via respective coaxial cables, which may provide power and control of the cameras (by the ECU) and which may provide image data from the cameras to the ECU, and which may provide video images from the ECU to the display devices. Each device (e.g., camera and display device) is thus connected to and communicates with the ECU via a single respective coaxial cable, thus reducing cable inputs to the video mirror display and the center stack display. The connections and communications may utilize aspects of the systems described in U.S. Pat. Nos. 10,264,219; 9,900,490 and/or 9,609,757, which are hereby incorporated herein by reference in their entireties.

The ECU may selectively or episodically provide video images to the center stack display or head unit 22 and/or the video mirror display 20 based on vehicle speed, user actuatable input (such as via a human machine interface (HMI) or the like), and/or a driving condition of the vehicle. For example, at slower speeds (e.g., during a parking or unparking maneuver), video images (such as surround view images or rearview images or the like) are displayed at the center stack display 22 (where it is safe for the driver to look down toward the center stack display when slowly maneuvering the vehicle), and at higher speeds (such as when the vehicle is driven forward along a road), video images (such as rearview images or CMS images or the like) are displayed at the video mirror display 20 (where it is safe for the driver to view without taking his or her eyes off the road when driving the vehicle at higher speeds). The system may also selectively display images at the center stack display 22 or video mirror display 20 responsive to a user actuatable input or a driving condition of the vehicle (such as to provide an alert or display an object in the path of the vehicle).

The ECU may, during forward travel, and via processing of image data captured by at least the plurality of CMS cameras, generate rearward view video images and may provide rearward view video images to the center console video display screen and to the video mirror display screen. Optionally, the rearward view video images provided to and displayed at the center console video display screen may provide different rearward views to the driver of the vehicle as compared to the rearward views provided by the rearward view video images provided to and displayed at the video mirror display screen. For example, the driver may adjust one of the views (e.g., adjust the video images displayed at the console downward) while the other view (the video images displayed at the mirror video display screen) are not adjusted or otherwise adjusted by the driver.

Thus, video images representative of different rearward views for display at the center console video display screen and at the video mirror display screen may be derived from the same set of captured image data or may be derived from different sets of captured image data (image data captured by different cameras or different sets of cameras). Video images representative of different rearward views derived from the same set of captured image data (i.e., different regions of the field(s) of view of the same camera(s)) may be displayed at the center console display screen and video mirror display screen by processing, at the ECU, different portions of the same set of captured image data and communicating the generated video image signals representative of the different portions of image data from the ECU to the different display screens, and/or by processing, at the ECU, the entire set of captured image data and then communicating different video image signals representative of different portions of the processed image data from the ECU to the center console and video mirror display screens. Optionally, video images representative of different rearward views and derived from different sets of image data (such as derived from image data captured by the rearward viewing surround view camera and image data captured by the rearward viewing CMS camera) may be displayed at respective ones of the center console display screen and video mirror display screen by processing, at the ECU, different sets of captured image data (captured by different camera(s)) and communicating the generated video image signals representative of different rearward views and derived from the different sets of captured image data to the respective displays.

When the vehicle is traveling rearward, the ECU, via processing of image data captured by at least the plurality of surround view cameras, generates surround view video images and provides the surround view video images to the center console display screen and may also provide surround view video images to the video mirror display screen. The surround view video images provided to the center console video display screen may provide different surround views to the driver as compared to the surround views provided to the driver by the surround view video images displayed at the video mirror display screen. For example, the center console video display screen may display surround view video images derived from image data captured by all of the surround view cameras (such as in a top down or bird's eye view), while the driver may select or adjust the video mirror display screen to display video images derived from image data captured by only one of the surround view cameras (such as a side surround view cameras to further assist the driver in parking the vehicle).

Thus, video images representative of different surround views for display at the center console video display screen and video mirror display screen may be derived from the same set of captured image data or from different sets of captured image data (image data captured by different cameras or different sets of cameras). Video images representative of different surround views and derived from the same set of captured image data (i.e., different regions of the field(s) of view of the same camera(s)) may be displayed at the center console display screen and video mirror display screen by processing, at the ECU, different portions of the same set of captured image data and communicating the generated video image signals representative of the different portions of image data from the ECU to the different display screens, and/or by processing, at the ECU, the entire set of captured image data and then communicating different video image signals representative of different portions of the processed image data from the ECU to the different display screens. Optionally, video images representative of different surround views and derived from different sets of captured image data (such as derived from image data captured by the rearward viewing surround view camera and image data captured by one of the side surround view cameras) may be displayed at respective ones of the center console display screen and video mirror display screen by processing, at the ECU, different sets of captured image data (captured by different camera(s)) and communicating the generated video image signals representative of different surround views and derived from the different sets of captured image data to the respective displays. For example, video images derived from image data captured by the rearward viewing surround view camera (the rear backup camera) may be displayed at the center console display screen during the reversing maneuver, while image data captured by all of the surround view cameras or by the side and/or front surround view cameras or by the rearward viewing CMS camera may selectively be displayed at the video mirror display screen during the reversing maneuver.

The rearward viewing camera 15c of the CMS cameras may also or otherwise function to provide rearward video images for a dual-mode interior rearview video mirror that can switch from a traditional reflection mode to a panoramic live-video display mode, such as by utilizing aspects of the mirror assemblies and systems described in U.S. Pat. Nos. 10,442,360; 10,421,404; 10,166,924 and/or 10,046,706, and/or U.S. Publication Nos. US-2020-0377022; US-2019-0258131; US-2019-0146297; US-2019-0118717 and/or US-2017-0355312, and/or U.S. patent application Ser. No. 16/949,976, filed Nov. 23, 2020 and published May 27, 2021 as U.S. Publication No. US-2021-0155167, and/or Ser. No. 17/247,127, filed Dec. 1, 2020 and published Jun. 3, 2021 as U.S. Publication No. US-2021-0162926, and/or U.S. provisional applications, Ser. No. 63/199,858, filed Jan. 29, 2021, and/or Ser. No. 63/199,526, filed Jan. 6, 2021, which are all hereby incorporated herein by reference in their entireties.

Figure 2A:
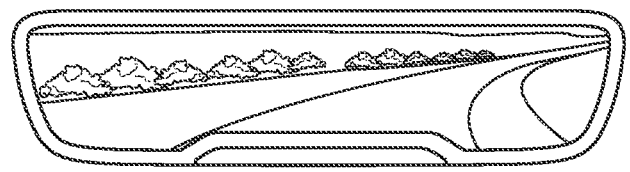
FIGS. 2A and 2B are views of an electro-optic interior rearview mirror assembly, with the display activated (FIG. 2A) and deactivated (FIG. 2B)
Figure 2B:
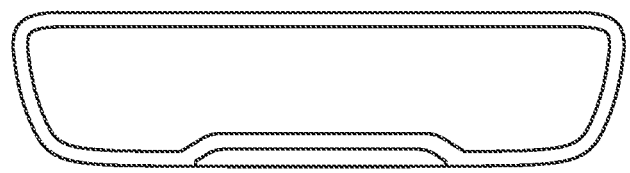
Figure 2C:
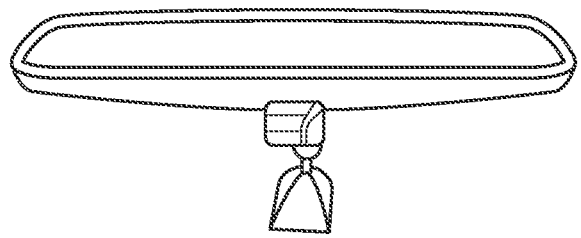
FIG. 2C is a perspective view of a prismatic interior rearview mirror assembly having a display device therein.

The interior rearview mirror assembly may comprise any suitable mirror assembly having a video display device disposed behind the mirror reflective element so as to be viewable through a partially reflectant and partially visible light transmitting or transflective mirror reflector of the mirror reflective element when the display screen is powered. For example, and such as shown in FIGS. 2A and 2B, the interior rearview mirror assembly may comprise an auto-dimming electro-optic (such as electrochromic) mirror assembly that operates as a reflecting mirror (FIG. 2A) when the display screen is off, and functions as a video mirror (FIG. 2B) when the display screen is activated. Optionally, and such as shown in FIG. 2C, the mirror assembly may comprise a prismatic mirror reflective element (that is toggled between a daytime viewing position and a nighttime or anti-glare viewing position) having a video display screen disposed behind the transflective mirror reflector of the prismatic mirror reflective element.

Thus, when the mirror assembly is set to the video display mode (such as via actuation by the driver of a user-actuatable input), the ECU automatically switches to communicate video images derived from image data captured by the rearward viewing camera 15c to the video display screen at the interior rearview mirror.

Optionally, for a pickup truck application (such as shown in FIG. 1), the system may include a truck bed camera 26 disposed at the rear of the cab of the vehicle and having a field of view that encompasses the truck bed. The ECU communicates with the bed camera 26 and receives image data captured by the truck bed camera 26 and provides video images (derived from image data captured by the truck bed camera 26) to the center stack display 22, such as responsive to actuation by the driver of a user-actuatable input in the vehicle.

Figure 3:
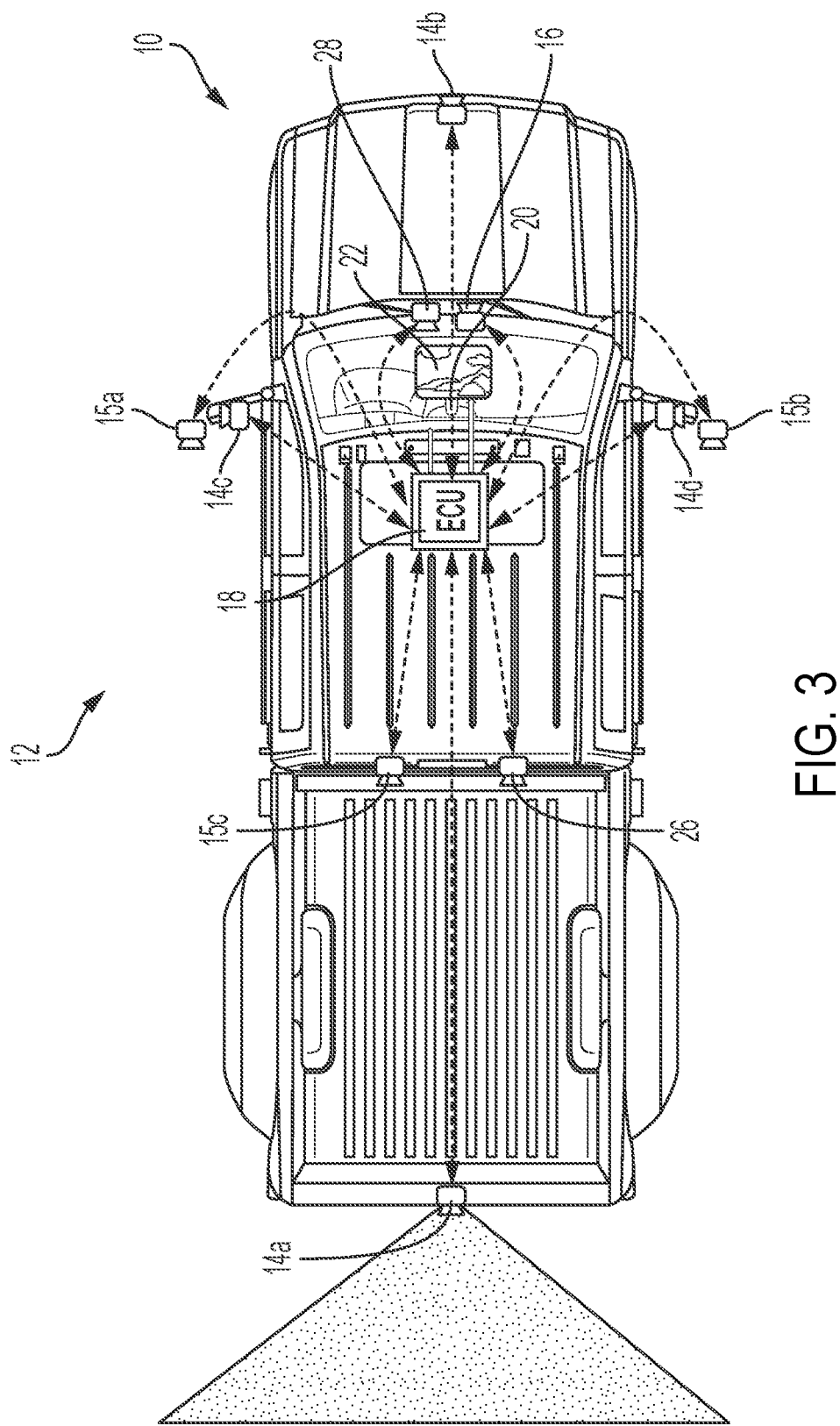
FIG. 3 is a plan view of another vehicle, which includes the system of FIG. 1 along with driver monitoring capabilities.

Optionally, and such as shown in FIG. 3, the system may include a driver monitoring camera 28 disposed in the vehicle cabin with a field of view encompassing the head or face or eyes of the driver of the vehicle. The ECU communicates with the driver monitoring camera 28 and receives image data captured by the driver monitoring camera 28 and processes the received captured image data to determine a degree of driver attentiveness or driver drowsiness or driver distraction. The in-cabin camera that views the driver's head can be used to detect driver head position change. Optionally, the displayed video images being displayed may be adjusted or panned accordingly to mimic what the driver would see looking at different angles at an exterior side view mirror or at the interior rearview mirror.

Figure 4:
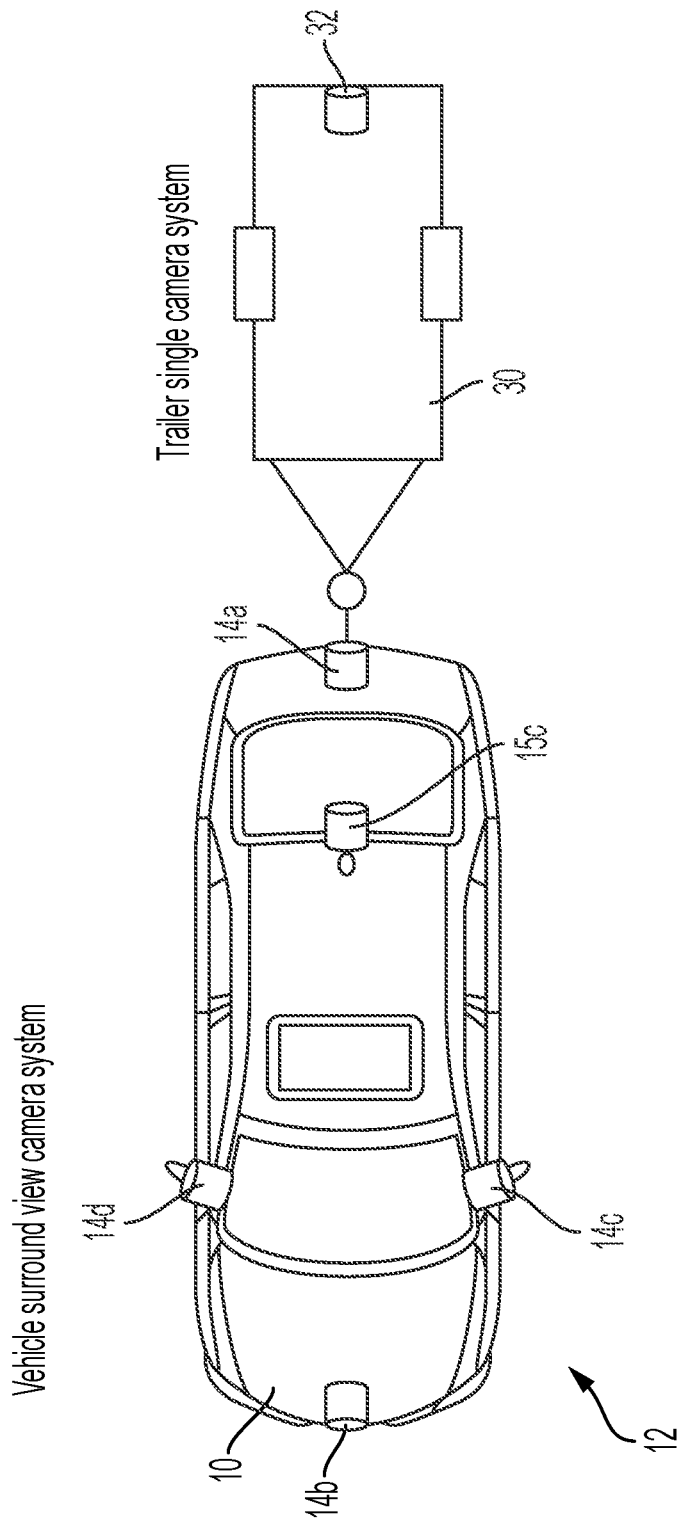
FIG. 4 is a plan view of the vehicle, showing the vehicle towing a trailer.
Figure 5:
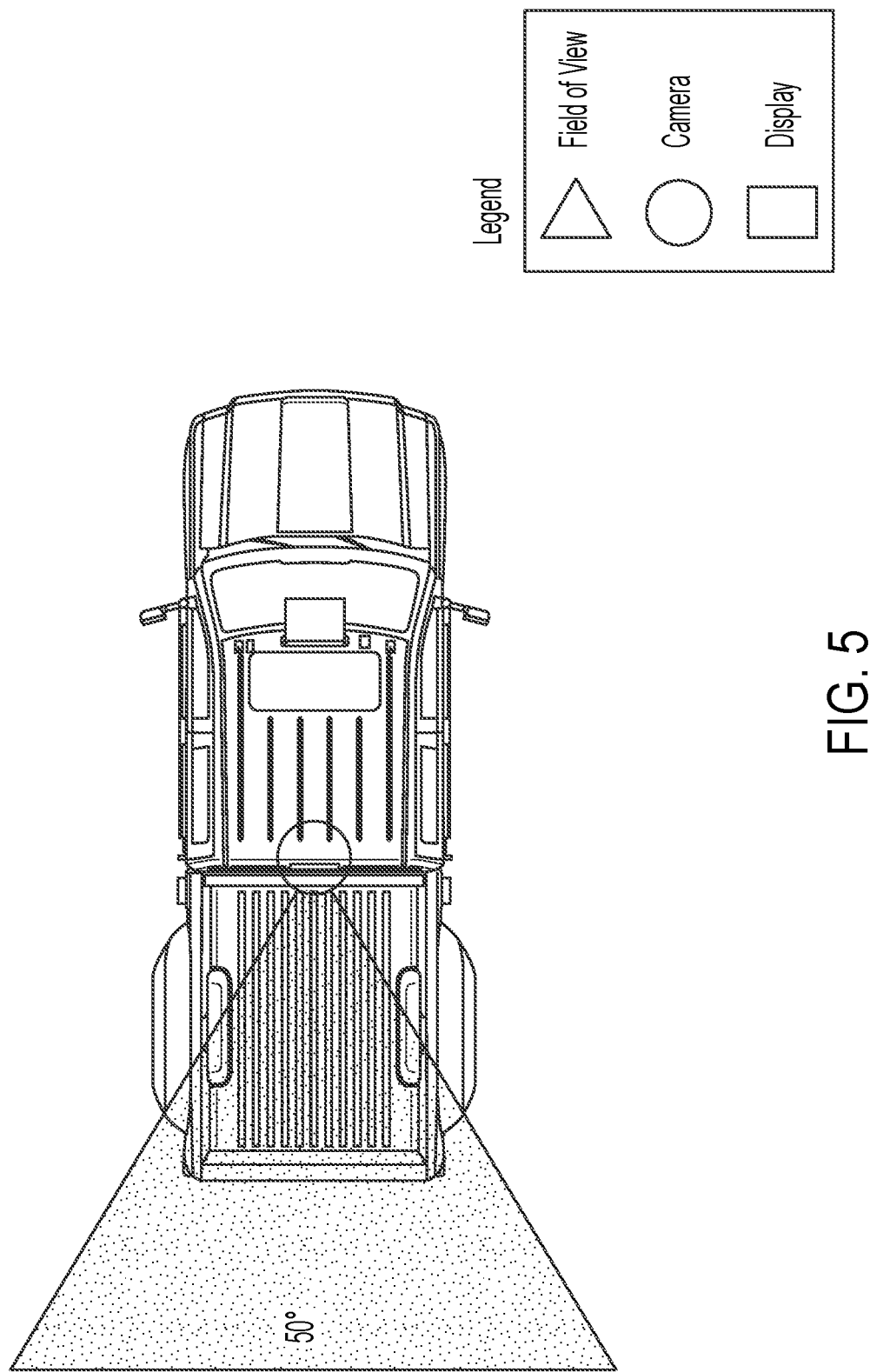
FIGS. 5-8 are plan views of vehicles, showing different camera monitoring systems.
Figure 6:
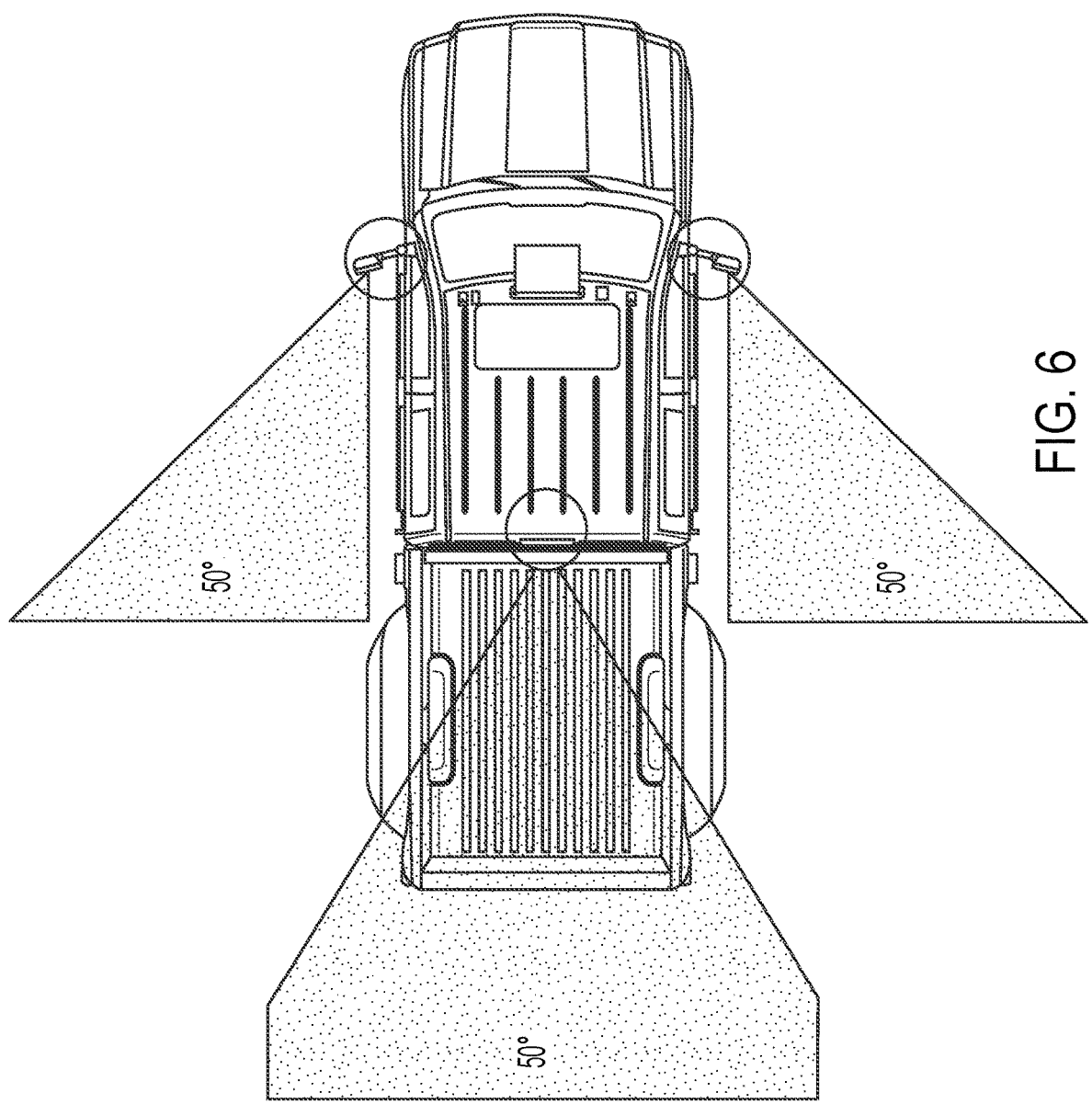
Figure 7:
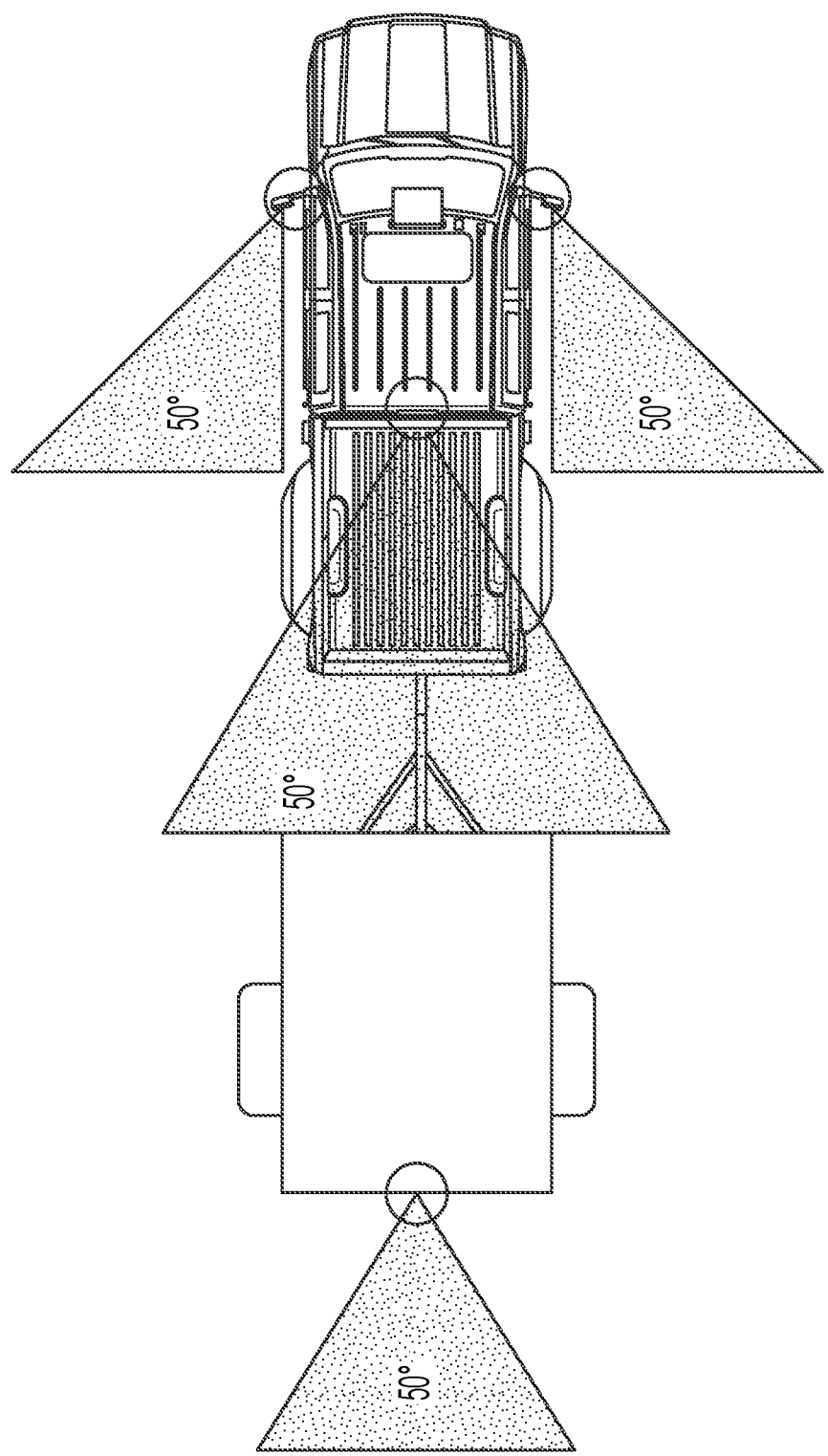

Optionally, and such as shown in FIG. 4, the vehicle may include a trailering assist function that is operable to assist in maneuvering (such as backing up or reversing) the vehicle with a trailer 30 hitched to the vehicle at a hitch at the rear of the vehicle. The system communicates (such as via wireless communication or via a wired link) with a rearward viewing camera 32 disposed at a rear of the trailer. The rear trailer camera 32 is disposed at the rear portion of the trailer, such as at the back end of the trailer, with the trailer camera centrally located at the rear portion and having a field of view at least rearward (and downward) rearward of the trailer. The rear trailer camera may be suitable for use as a trailer backup camera or a surround-view camera, or may be disposed at or near an upper region of the rear (and/or sides) of the trailer to provide a more optimal rearward view to the driver (for a CMS application) when the vehicle tows the trailer in a forward direction.

The ECU receives image data captured by the rear trailer camera 32. The ECU, via processing of the received image data captured by the rear trailer camera, may detect objects or the like and/or may generate a video image output to display video images of the scene rearward of the trailer at the video mirror display or the center stack display for viewing by the driver of the vehicle. Optionally, the system may include or communicate with multiple trailer cameras (such as sideward viewing cameras and a forward viewing camera) to provide a surround view display of areas around the trailer as well as the vehicle, such as by utilizing aspects of the systems described in U.S. patent application Ser. No. 17/031,956, filed Sep. 25, 2020 and published Apr. 1, 2021 as U.S. Publication No. US-2021-0094473, which is hereby incorporated herein by reference in its entirety. The system thus may display a 360 degree bird's eye view or surround view of the surroundings of the towing vehicle and the trailer being towed by the vehicle.

Optionally, the system may provide for display of a trailer see-through image (such as by utilizing aspects of the systems described in U.S. patent application Ser. No. 17/031,956, incorporated above), which shows a rearward and transparent view through the trailer with seamless stitching of video images and image data captured by the towing vehicle's rear backup camera with video images and image data captured by the trailer or satellite camera to provide the rearward video images. For example, the ECU may process image data captured by the rearward viewing trailer camera 32 and image data captured by some or all of the rearward viewing CMS cameras 15a-c to generate the composite video images for display at the center stack display and/or the video mirror display.

The ECU may selectively or episodically provide the generated composite video images to the center stack display and/or the mirror display, such as responsive to a user actuatable input or responsive to a vehicle driving condition or responsive to vehicle speed or the like. For example, the ECU may provide the generated composite see-through trailer images to the center stack display when the vehicle is being driven in reverse and/or when the vehicle (towing the trailer) is driven forward at a speed below a threshold speed (such as 7 mph or 10 mph or 15 mph or the like), and then may automatically switch to provide the generated composite see-through trailer images to the video mirror display when the vehicle is being driven forward at a speed above the threshold speed (such as 7 mph or 10 mph or 15 mph or the like). Thus, when the vehicle (towing the trailer) is traveling at greater speeds, the video images are displayed at the mirror assembly so that the driver of the vehicle can readily view them without taking his or her eyes off the road.

The trailer assist system or trailer surround view display system may utilize aspects of the systems described in U.S. Pat. Nos. 9,446,713; 9,085,261 and/or 6,690,268, and/or U.S. Publication Nos. US-2020-0017143; US-2019-0297233; US-2019-0347825; US-2019-0118860; US-2019-0064831; US-2019-0042864; US-2019-0039649; US-2019-0143895; US-2019-0016264; US-2018-0276839; US-2018-0276838; US-2018-0253608; US-2018-0215382; US-2017-0254873; US-2017-0217372; US-2017-0050672; US-2015-0217693; US-2014-0160276; US-2014-0085472 and/or US-2015-0002670, which are all hereby incorporated herein by reference in their entireties.

The ECU provides a central and common image processor for processing image data captured by any one or more of the vehicle (and trailer) cameras. The cameras communicate with the ECU over any suitable communication link, such as via Texas Instrument's FPD-LINK III, or Maxim Integrated's GMSL2, low voltage differential signaling (LVDS), or ethernet, or such as a CAN bus or LIN bus or I2C or the like. The ECU provides video images to the center stack display (head unit) or to the interior video mirror, and may switch between the two based on a driving condition of the vehicle, user-actuatable input, and/or vehicle speed. The interior mirror assembly may comprise a dual mode mirror having a full mirror display screen and may also be selectively actuated to provide a reflected view rearward of the vehicle or a video image display of images rearward of the vehicle. The ECU provides the rearward images to the mirror display responsive to actuation of a user input in the vehicle.

The data processor or image processor of the ECU is capable of receiving image data from each of the cameras and processing the received image data for generating video images and/or for object detection or the like. Thus, the ECU has multiple image data input ports for receiving the image data from the respective cameras and for communicating to and/or controlling the respective cameras (such as to instruct the cameras to capture image data and/or to control various camera parameters). The image processing of image data captured by multiple cameras for multiple systems (e.g., a backup assist system, a surround view vision system, a rearview display system, a CMS system, a driver monitoring system, a truck bed viewing system and the like) is thus performed at a single ECU of the vehicle, which allows for reduced processing capabilities (and reduced cost) at the video mirror display.

Optionally, the ECU may provide video images responsive to other vehicle systems, such as responsive to a lane-change assist system or blind zone monitoring system or the like. For example, the ECU may provide video images to the video screen of the interior video mirror responsive to vehicle approach in a side lane only when a lane change maneuver of the equipped vehicle is anticipated (such as by the driver activating a turn signal indicator or such as by a camera vision-based lane departure warning system of the equipped vehicle detecting a lane change maneuver or such as by a driver monitoring camera detecting eye movements or head movements of the driver indicative of the driver checking mirrors and/or blind spots in anticipation of making a lane change). In this regard, use can be made of the systems described in U.S. Pat. No. 10,300,856, which is hereby incorporated herein by reference in its entirety.

Figure 8:
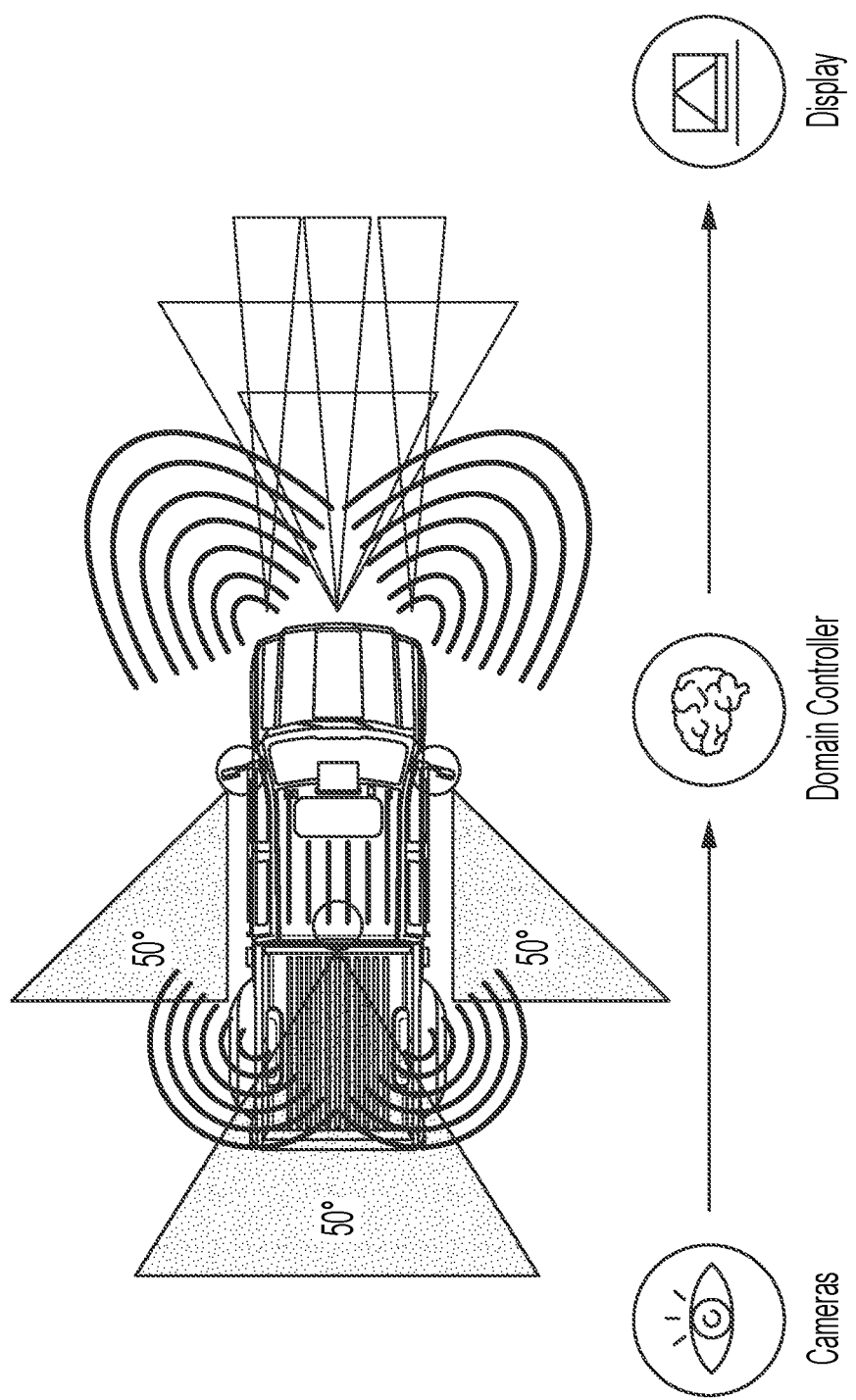
Figure 9C:
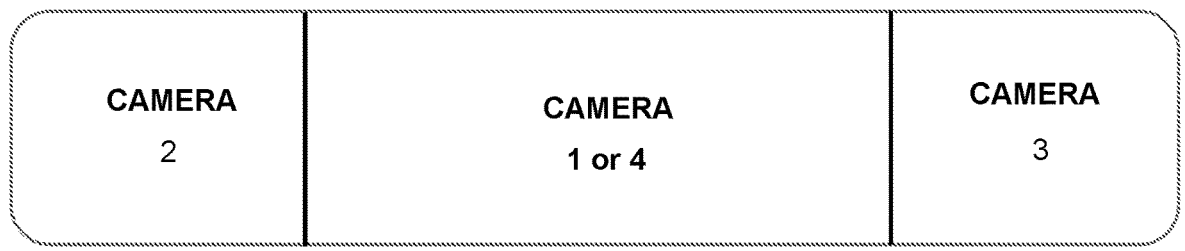
FIGS. 9A-C are views of the mirror display, showing display configurations for displaying video images derived from image data captured by different cameras of the vision system.
Figure 9B:
Figure 9A:
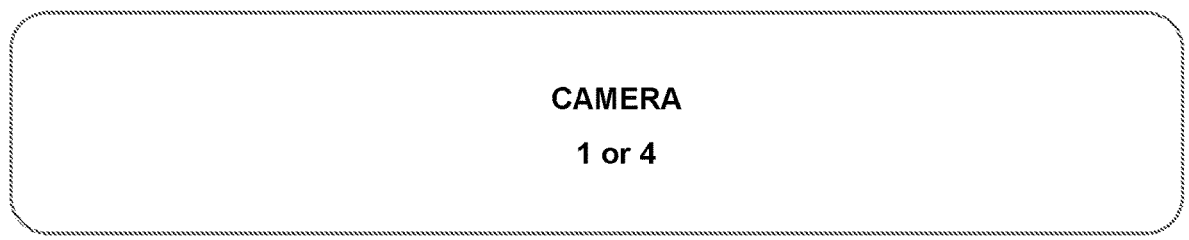

With reference to FIGS. 5-8, the vehicle may have a rearward viewing camera disposed at a CHMSL (center high mounted stop lamp) area for capturing video image data for displaying video images a the interior mirror display (FIG. 5), or may also include side-mirror mounted cameras (FIG. 6), and/or may include a trailer mounted rearward viewing camera at a trailer hitched to and towed by the vehicle (FIG. 7), and the controller or ECU may receive outputs of other cameras and/or sensors of the vehicle, such as radar sensors and/or ultrasonic sensors and/or forward viewing cameras and/or the like (FIG. 8). The video display screen is operable to display video images captured by one or more of the cameras. For example, the video display screen may provide a single video image display (FIG. 9A), such as for displaying video images derived from image data captured by the rearward viewing camera co-located at the CHMSL area (represented as camera 1) or by the trailer camera (represented as camera 4) during forward driving of the vehicle or of the vehicle and trailer, or the video display screen may provide the single video image display for displaying video images derived from image data captured by the rear backup camera or by the rearward viewing trailer-mounted camera during a backing-up maneuver of the vehicle or of the vehicle and trailer (where the rear backup camera is used for display when the vehicle is not towing a trailer and the rearward viewing trailer-mounted camera is used for display when the vehicle is towing a trailer). During a backing-up maneuver of the vehicle, the rear backup camera is used for display of video images, and during a backing-up maneuver of the trailer hitched to the vehicle, the trailer camera (such as a lower portion of the view of the trailer camera) is used for display of video images. The video display screen may operate to provide a split screen display (FIG. 9B), such as for displaying video images derived from image data captured by the two side-mounted rearward and sideward viewing cameras (such as for a CMS system) represented as cameras 2 and 3, respectively, and/or the video display screen may operate to provide a split screen display (FIG. 9C), such as for displaying video images derived from image data captured by the two side-mounted rearward and sideward viewing cameras and with a central pane of video images derived from image data captured by the rearward viewing camera at the CHMSL area or the rearward viewing trailer-mounted camera (such as for a CMS system).

Figure 10:
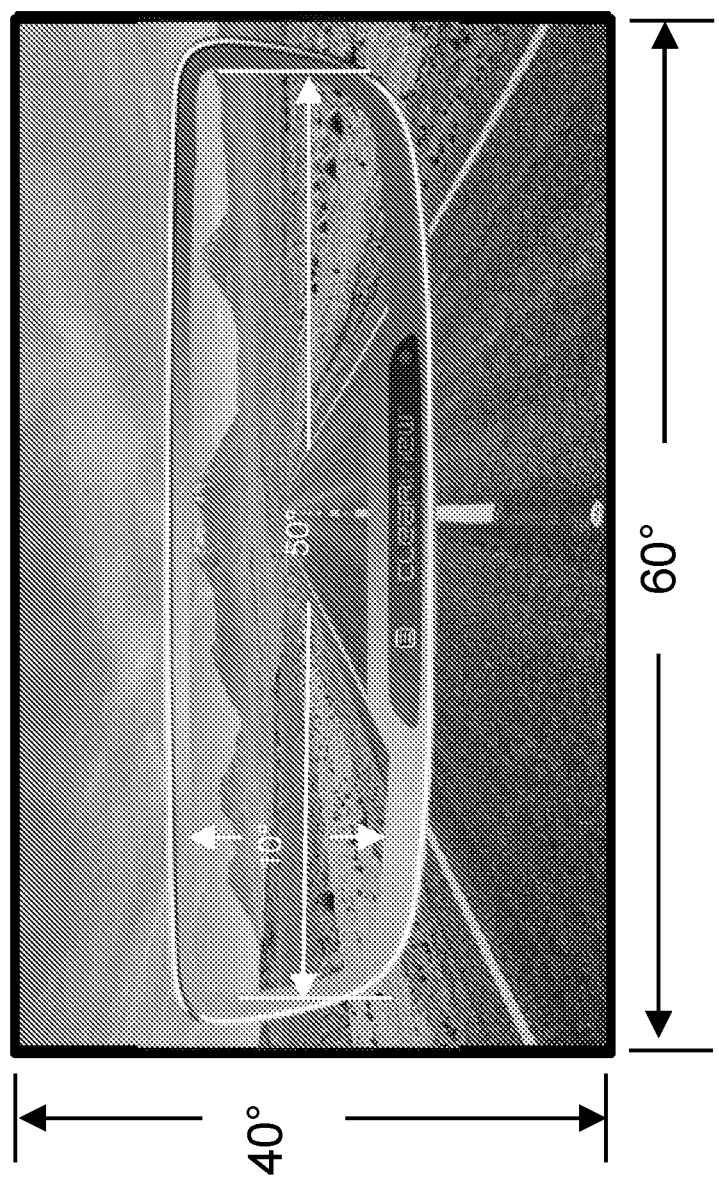
FIG. 10 is a view showing the camera's view and the portion of the camera's view that is displayed at the mirror display.

As shown in FIG. 10, the rearward viewing camera (such as at the CHMSL area or at the trailer) may have a field of view that spans at least about 40 degrees vertically and at least about 55 degrees or 60 degrees horizontally. The displayed images are derived from only a portion or subset of the captured image data, and may provide displayed images that span about 10 degrees vertically and about 50 degrees horizontally. Changing the portion or subset of captured image data used to derive the displayed images allows the system to adjust the displayed images to various configurations within the overall captured image data.

Figure 11:
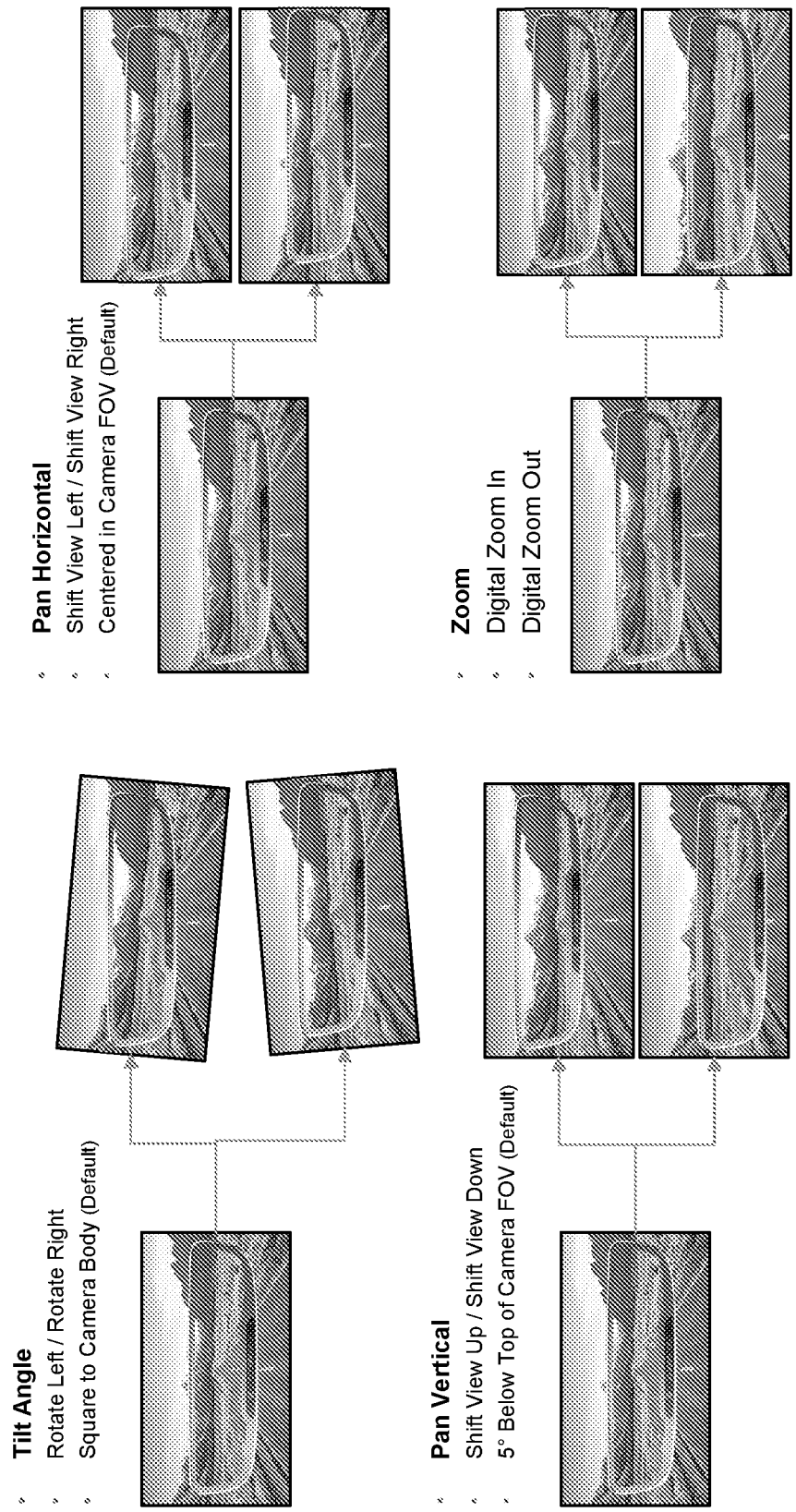
FIG. 11 shows various adjustments that can selectively be made by the driver of the vehicle to adjust the displayed image.

For example, and such as shown in FIG. 11, the system may allow for selective (selected by the driver) or automatic adjustments of the displayed images, such as by adjusting tilt angle, horizontal panning, vertical panning and/or zooming in/out. A driver may selectively adjust the display images, for example, based on the visibility provided by the camera position or the driver's seating configuration relative to the interior mirror display. Additionally or alternatively, the display may self-adjust to correct for a misalignment of the camera and/or orientation of the interior mirror display. For example, the system may pan, tilt, or rotate the images to match an orientation of the interior mirror display as adjusted by the driver of the vehicle. Thus, if the driver adjusts the mirror upward or downward or toward one side or the other, the displayed images are adjusted to display portions of the field of view of the camera that are representative of where the driver would be viewing if the driver were viewing reflections off of the mirror reflective element of the mirror assembly (with the video display screen deactivated).

The system may also adjust the displayed images based on a driving condition of the vehicle. For example, as the vehicle accelerates the display may pan up or zoom out to increase the visibility distance provided by the display or, as the vehicle decelerates the display may pan down or zoom in to provide a display representative of an area closer to the vehicle. Thus, the system may provide various field of view modes, including pan, tilt, roll, zoom, as well as graphical overlays and graphical icons by selectively adjusting or changing the portion or subset of captured image data from which the displayed images are derived and without changing the orientation of the camera or cameras capturing image data.

Figure 12C:
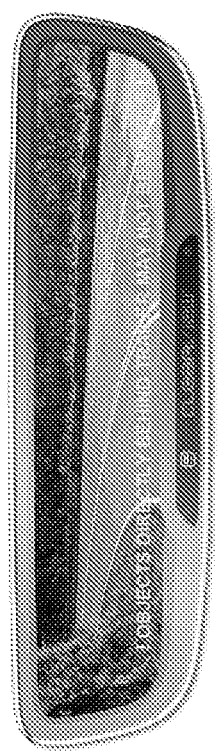
FIGS. 12A-C are views of the mirror, showing different display options when the vehicle is towing a trailer.
Figure 12A:
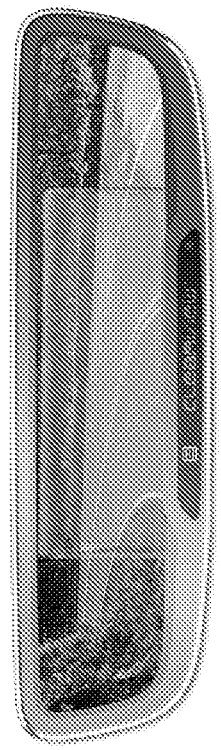
Figure 12B:
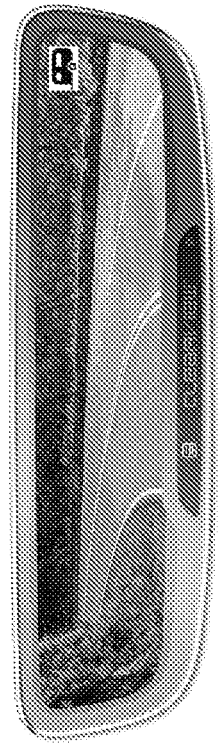

When towing a trailer, the system may provide optional or different display configurations. For example, the video display screen, when displaying video images derived from image data captured by the rearward viewing trailer camera at a trailer hitched to and being towed by the vehicle, may display a ghost image of the trailer (FIG. 12A) or may display a trailer icon (FIG. 12B) to remind the driver that the trailer is being towed by the vehicle. Optionally, during a reversing maneuver of the vehicle and trailer, the display screen (the mirror display screen and/or the center console display screen) may (while displaying video images derived from image data captured by the rearward viewing trailer camera) display a warning or alert to alert the driver that objects directly behind the trailer may not be visible in the displayed video images (see FIG. 12C). The reverse warning may be generated responsive to the vehicle being shifted into reverse and when the display is displaying the trailer camera images.

Figure 13:
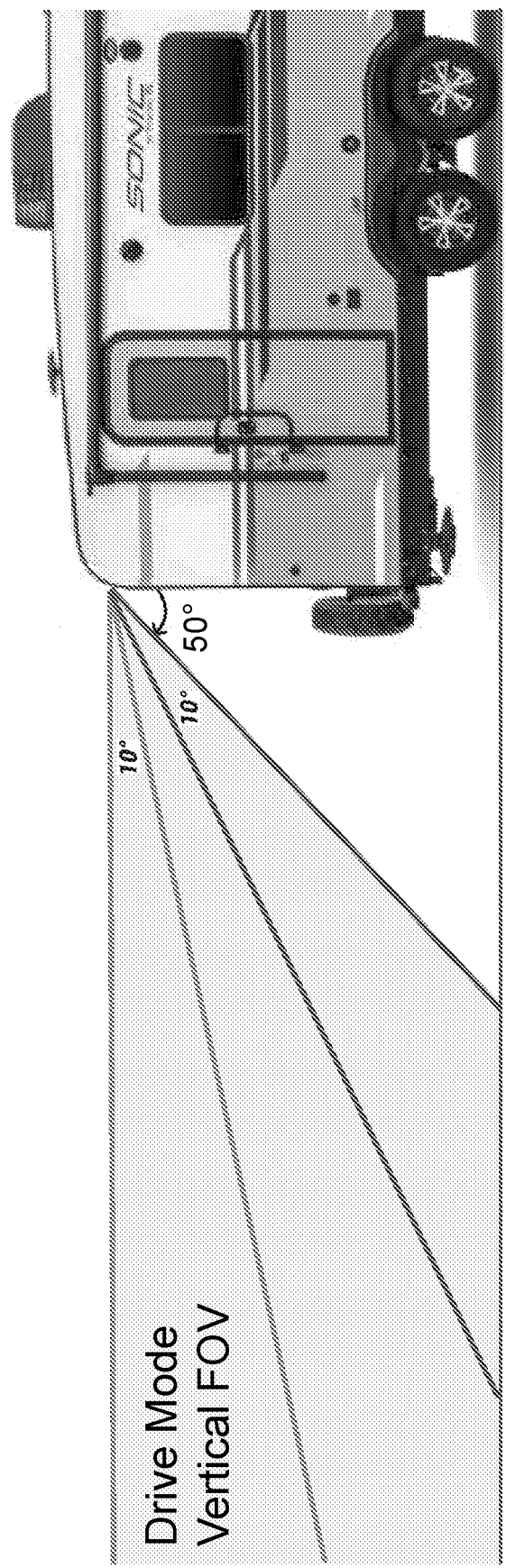
FIG. 13 is a side view of a trailer, showing the portions of the captured images used for displaying images at the display for the different operating conditions of the vehicle.
Figure 13B:
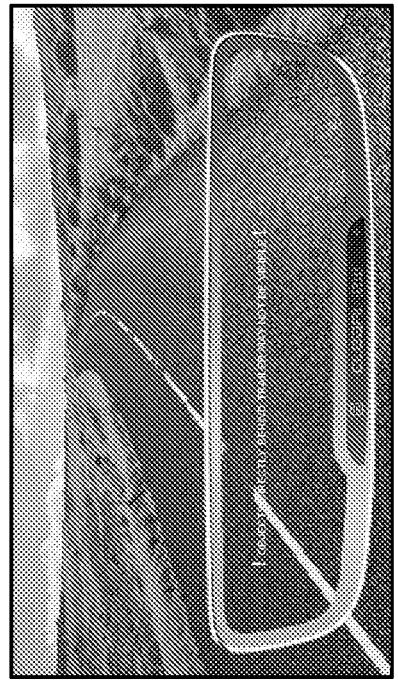
FIGS. 13A and 13B shows views of the camera captured image and a representation of the displayed image for different operating conditions of the vehicle.
Figure 13A:

Optionally, the system may automatically change or adjust the displayed images based on the driving mode of the vehicle towing the trailer. For example, the system may recognize when the trailer camera is connected and when in the trailer mode, the video display screen displays video images derived from image data captured by the trailer camera. When the vehicle is in park or drive, the displayed images may be derived from the upper third (or other suitable upper region) of the trailer camera's rearward field of view (see FIGS. 13 and 13A), and when the vehicle is shifted to reverse gear, the display pans down or otherwise changes automatically (such as via adjusting processing of the image data captured by the camera) to show the lower third (or other suitable lower region) of the trailer camera's rearward field of view (see FIGS. 13 and 13B), and may include a warning or alert as to the lack of visibility of detected objects immediately rearward of the trailer. Additionally or alternatively, the system may adjust the displayed images derived from image data captured by the trailer camera based on a user actuatable input, an orientation of the interior mirror display, and/or a driving condition of the vehicle. For example, the driver may provide an input to display the lower portion of the trailer camera's rearward field of view even when the vehicle is in a forward gear or drive (for forward driving) so that the driver may monitor an area closer to the rear of the trailer. Additionally, the system may adjust the display to match an orientation of the mirror or based on a driving condition of the vehicle.

Figure 14:
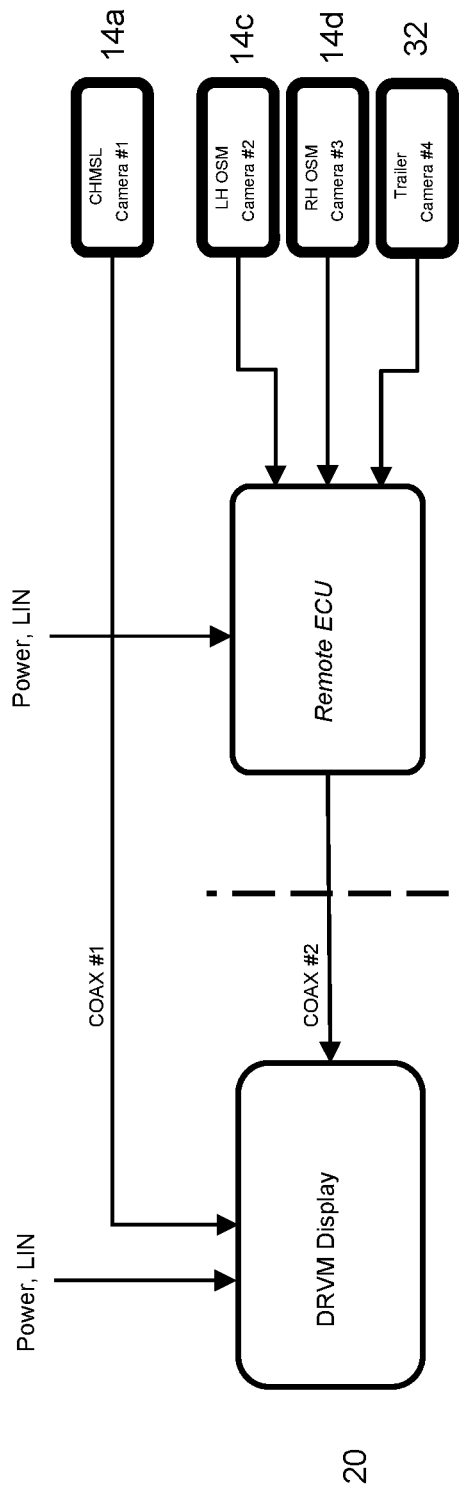
FIG. 14 is a block diagram of the vision system.
Figure 15:
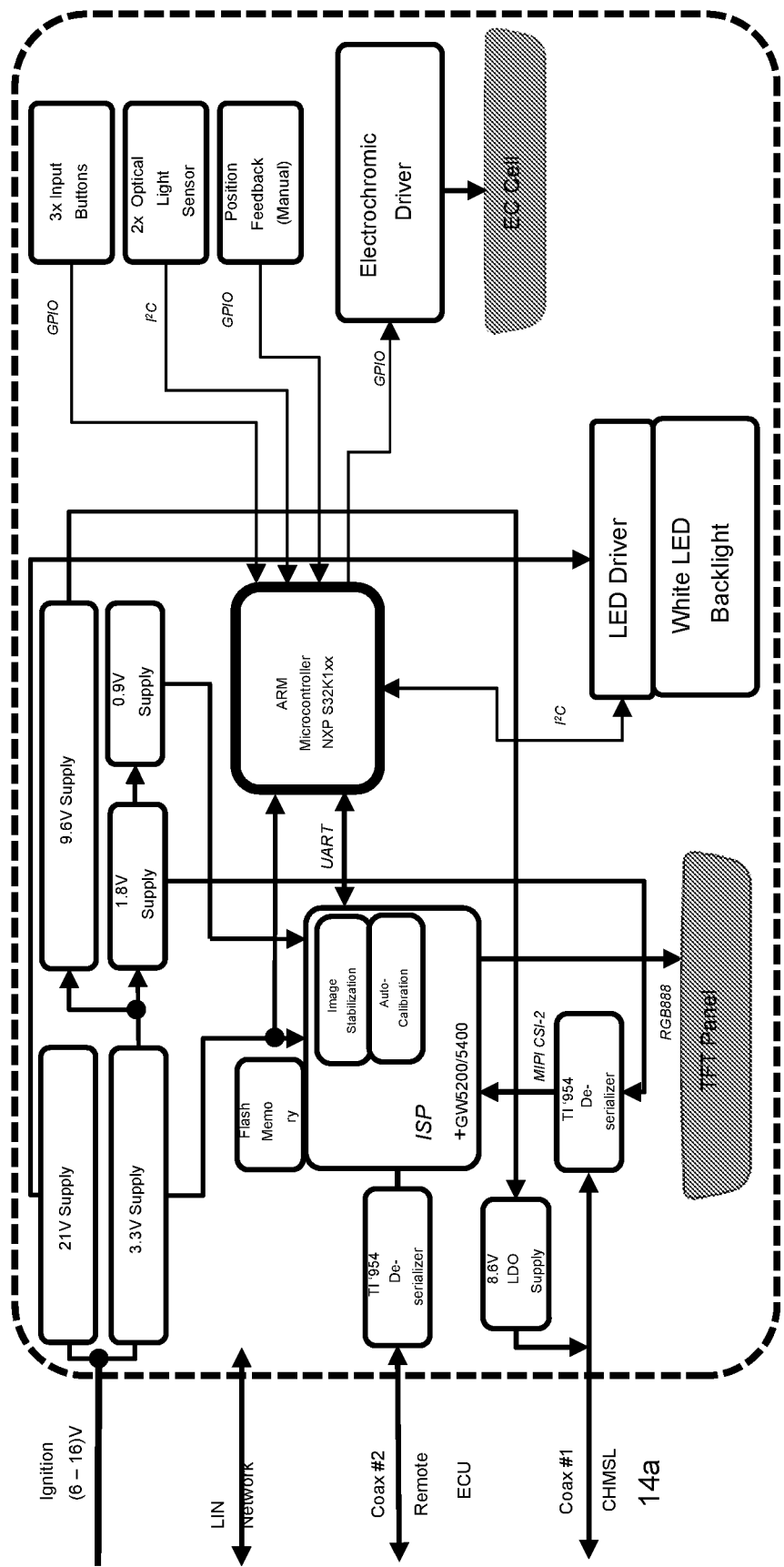
FIG. 15 is a block diagram of the mirror ECU of the system of FIG. 14.
Figure 16:
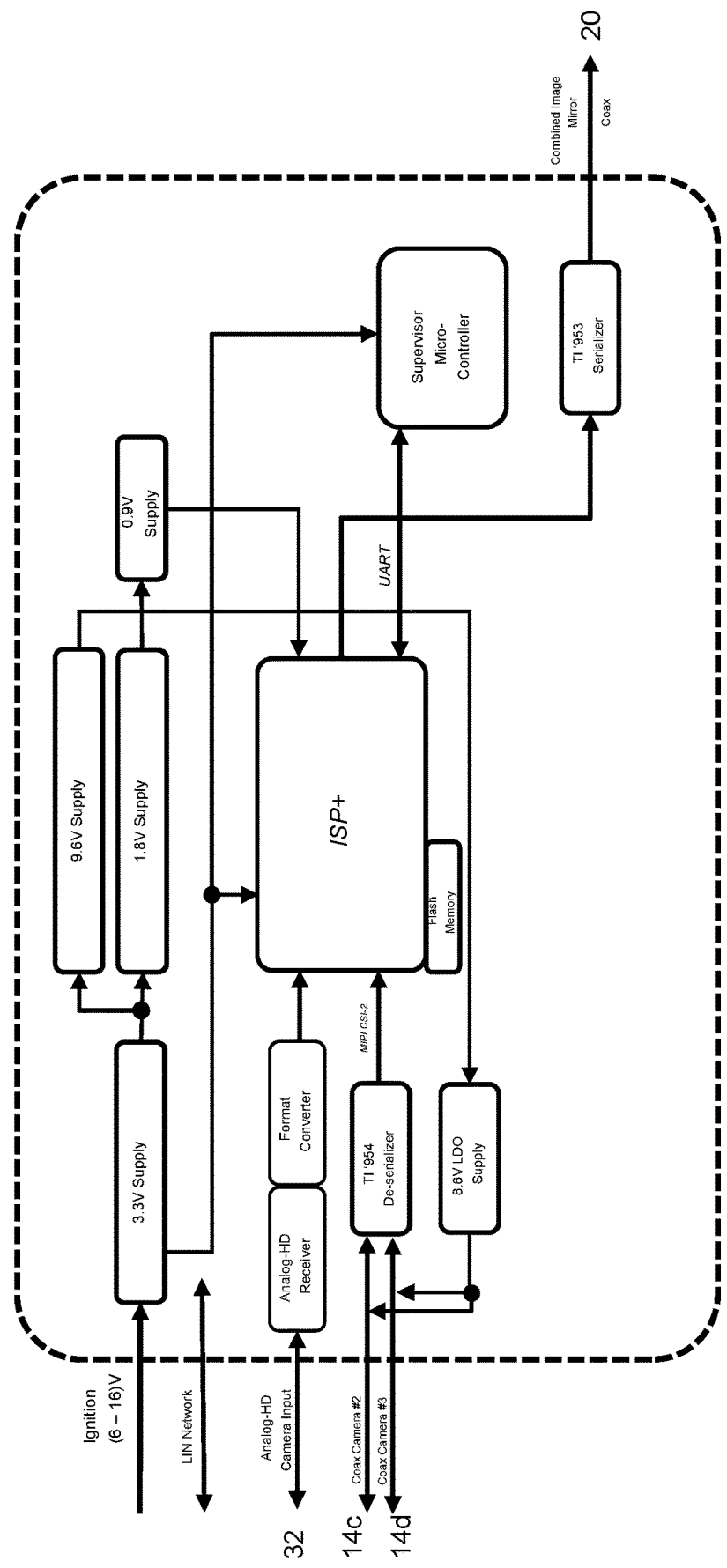
FIG. 16 is a block diagram of the remote ECU of the system of FIG. 14.

The vision system thus provides a video display that receives images or inputs from multiple cameras of the vehicle (and optionally from a trailer as well). The inputs may be provided from the rearward viewing camera or may be provided from a remote electronic control unit (ECU) that is separate and remote from the video display. For example, and with reference to FIG. 14, the vehicular rearview camera 14a may electrically connect to the video mirror display 20 via a first coaxial cable, while the side cameras 14c, 14d and the trailer camera 32 may electrically connect to a remote ECU, which electrically connects to the video mirror display 20 via a second coaxial cable. The mirror 20 includes a mirror ECU (FIG. 15) that receives inputs via the coaxial cables and provides the displayed video images and that controls dimming of the electrochromic mirror element. The remote ECU (FIG. 16) receives inputs from the trailer camera 32 (which may be an analog-HD camera or which may comprise a digital camera) and from the side cameras 14c, 14d and provides the combined image to the mirror 20 for display. Thus, the mirror ECU receives input from the vehicular rearview camera 14a via the first coaxial cable and input from the remote ECU (and thus side cameras 14c, 14d and trailer camera 32) via the second coaxial cable, thereby reducing the number of cables needed to enable communication between several cameras and/or ECUs.

Figure 17:
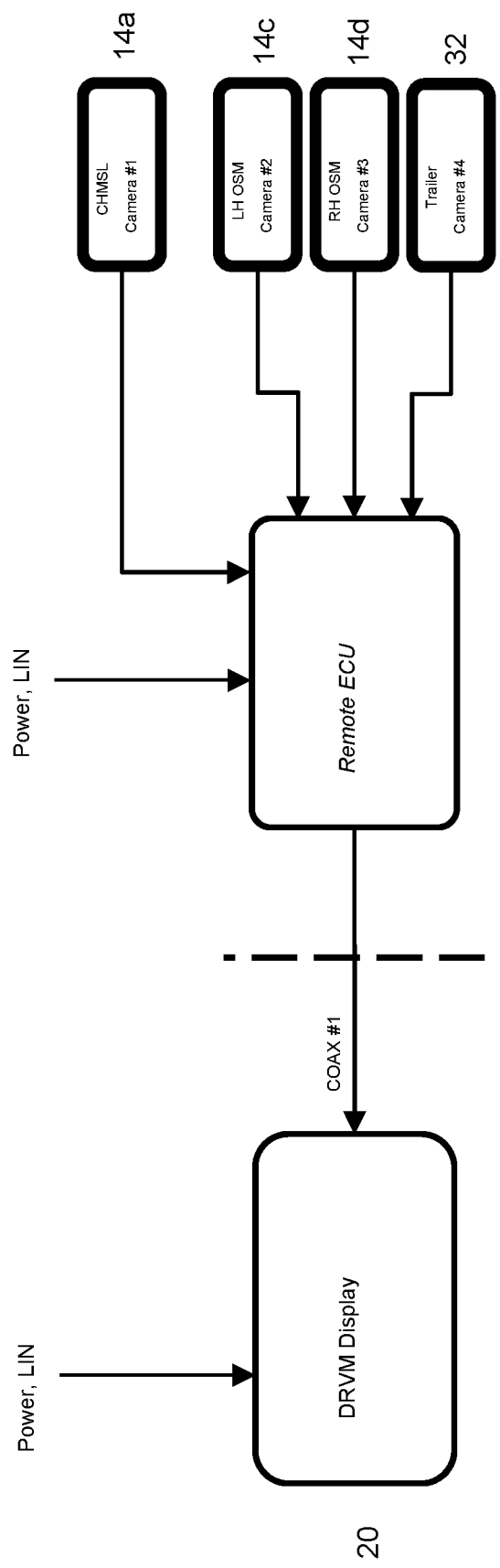
FIG. 17 is a block diagram of another vision system, with the CHMSL camera connecting to the remote ECU and with a trailer camera.
Figure 18:
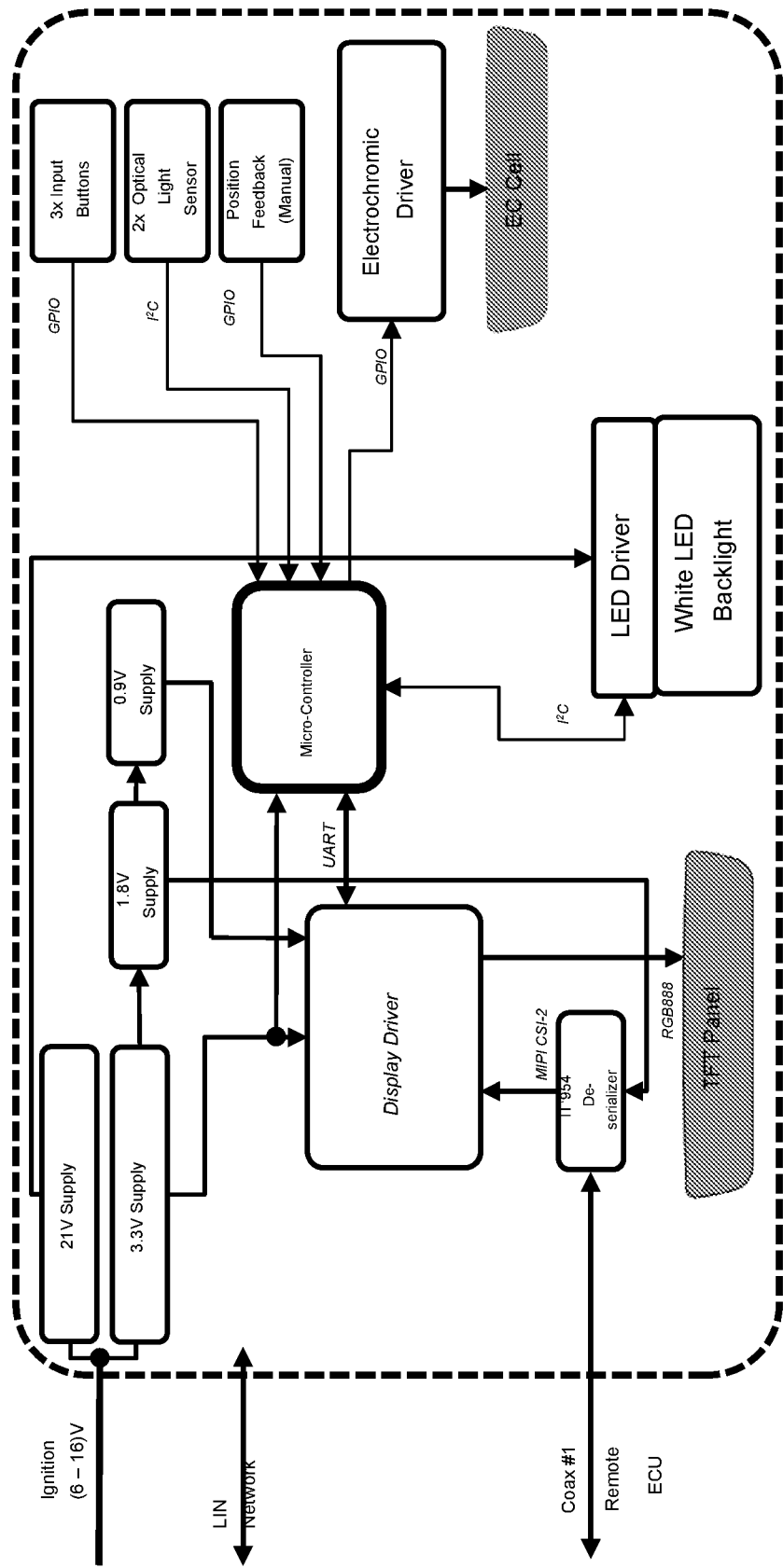
FIG. 18 is a block diagram of the mirror ECU of the system of FIG. 17.
Figure 19:
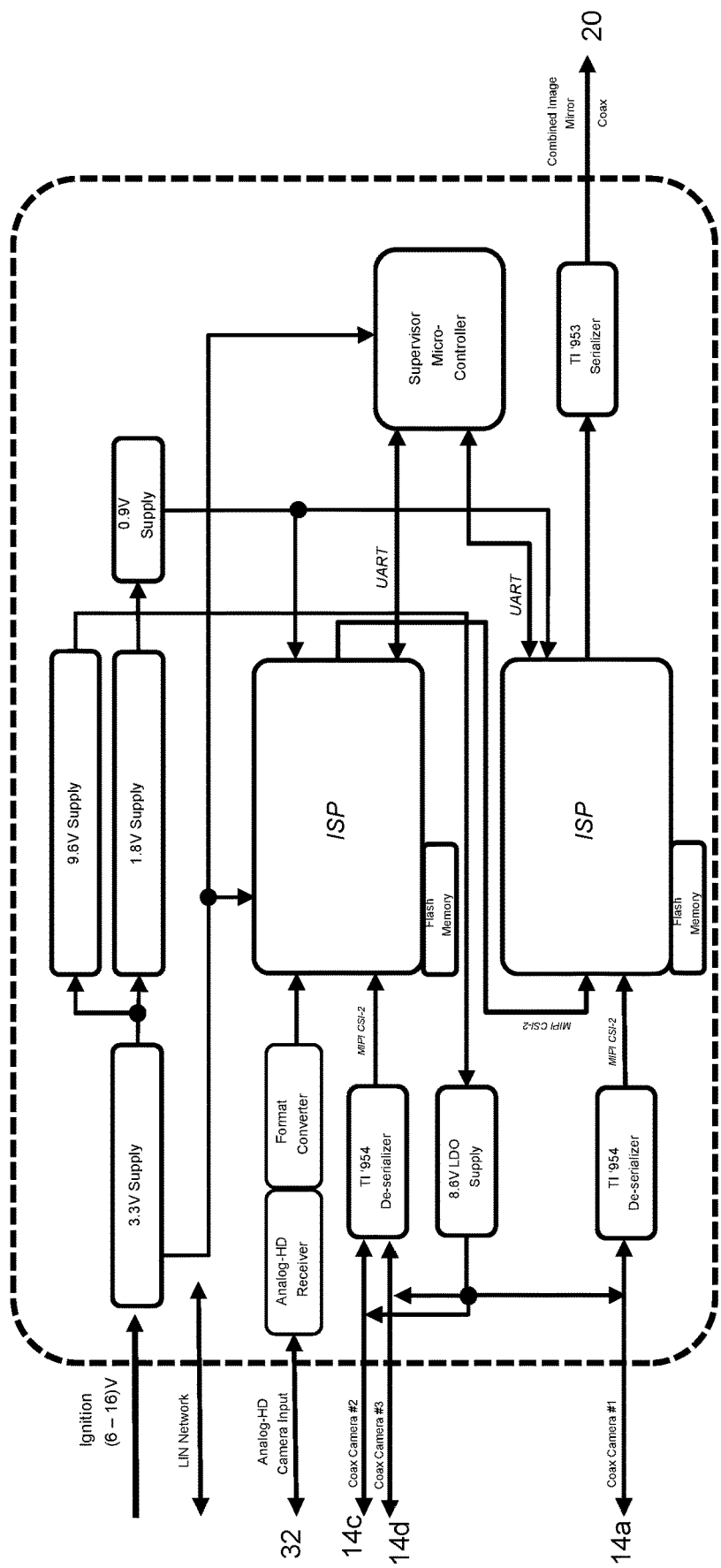
FIG. 19 is a block diagram of the remote ECU of the system of FIG. 17.

Optionally, the rearward viewing vehicle camera 14a may also provide its output to the remote ECU (FIG. 17), whereby a single coaxial cable electrically connects the remote ECU with the video mirror display 20. The mirror ECU (FIG. 18) receives the input via the single coaxial cable and provides the appropriate video display. The remote ECU (FIG. 19) receives inputs from each of the cameras and provides the combined image to the mirror 20 for display. Thus, in these implementations, the remote ECU receives inputs from the multiple cameras, combines the images and provides a single output to the video mirror display, further reducing the number of cables needed to connect to the video mirror display to enable communication between several cameras and/or ECUs and the video mirror display. The ECU at the video mirror display provides the displayed video images and controls dimming of the electrochromic mirror element.

Figure 20:
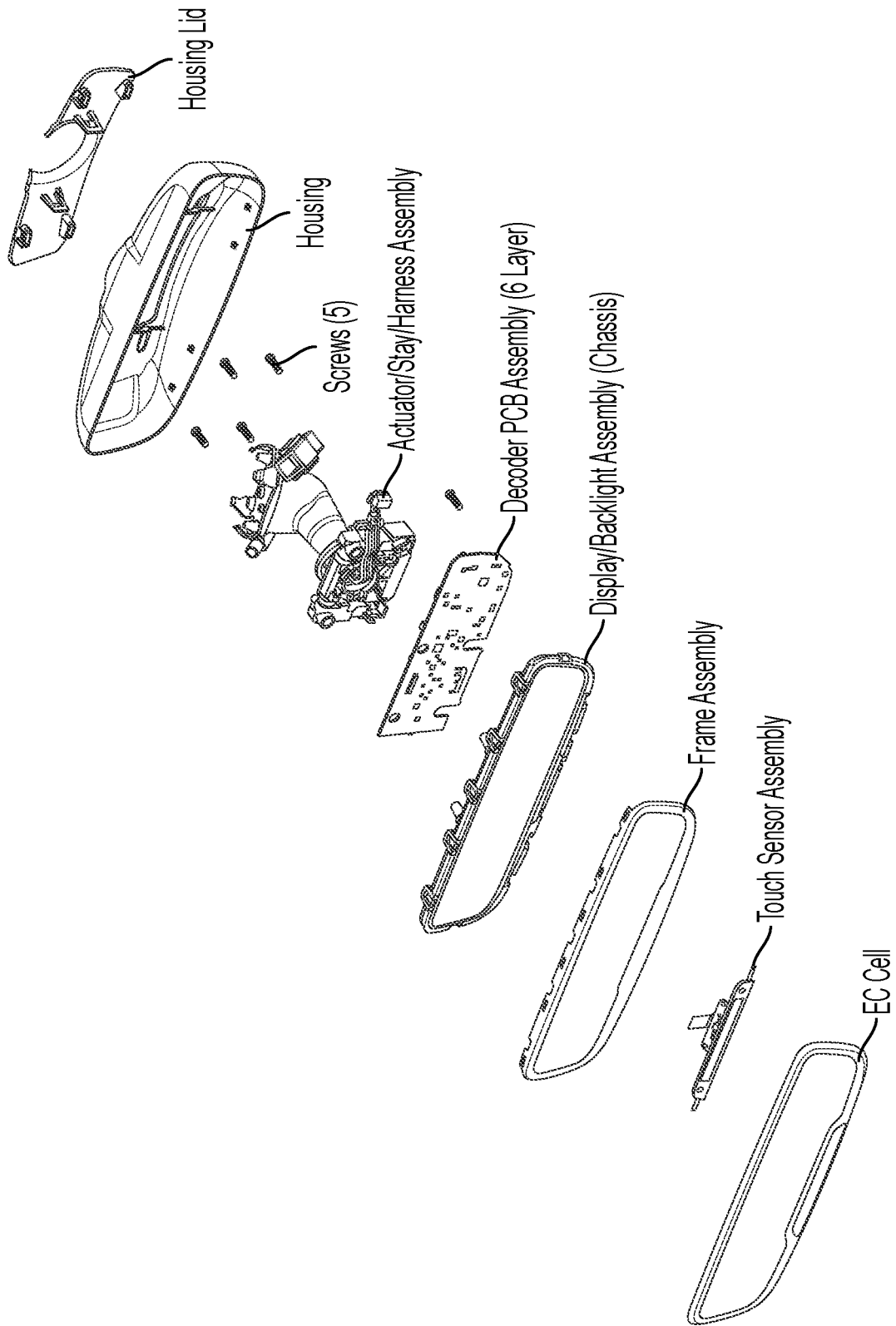
FIG. 20 is an exploded perspective view of the mirror assembly and display screen.
Figure 21C:
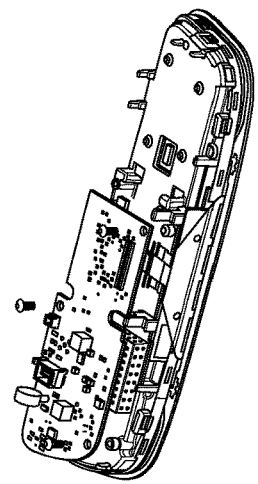
FIGS. 21A-E show process steps for assembling the mirror and display assembly.
Figure 21B:
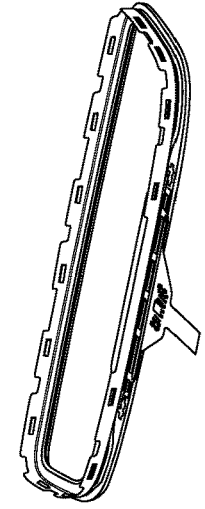
Figure 21A:
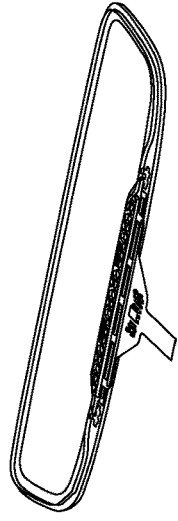
Figure 21E:
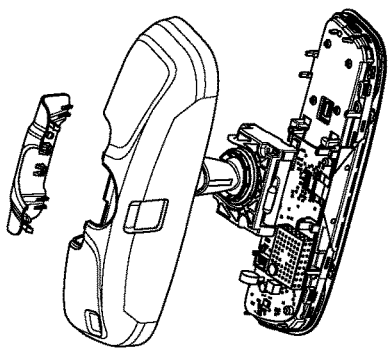
Figure 21D:
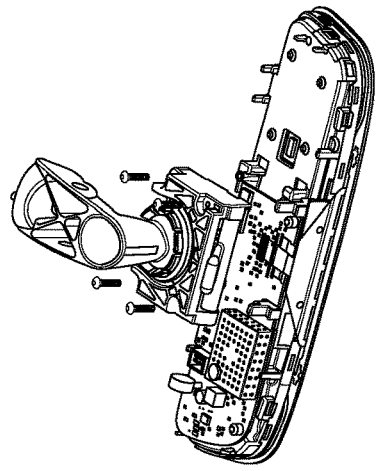
Figure 22:
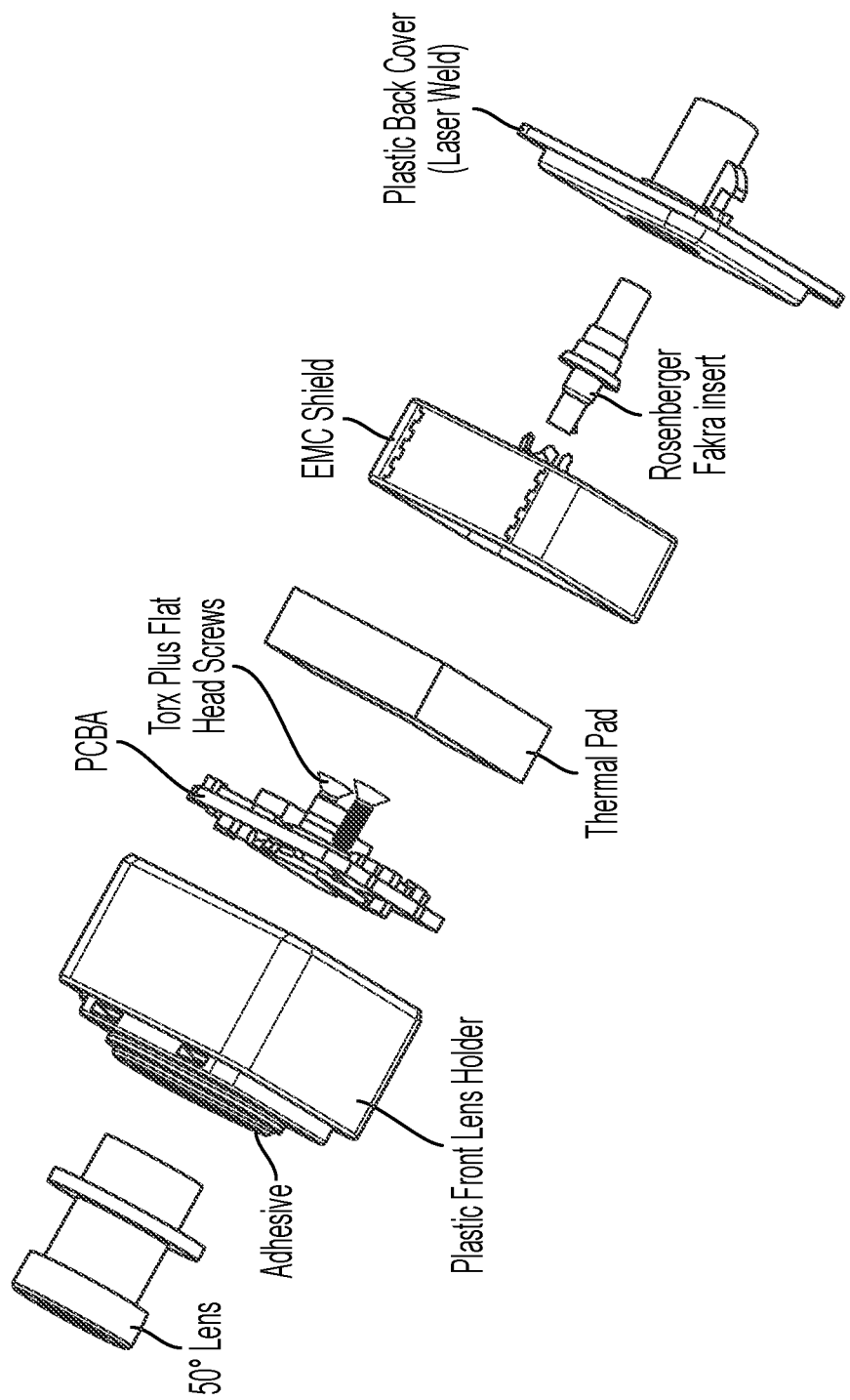
FIG. 22 is an exploded perspective view of a camera suitable for use with the system.
Figure 27:
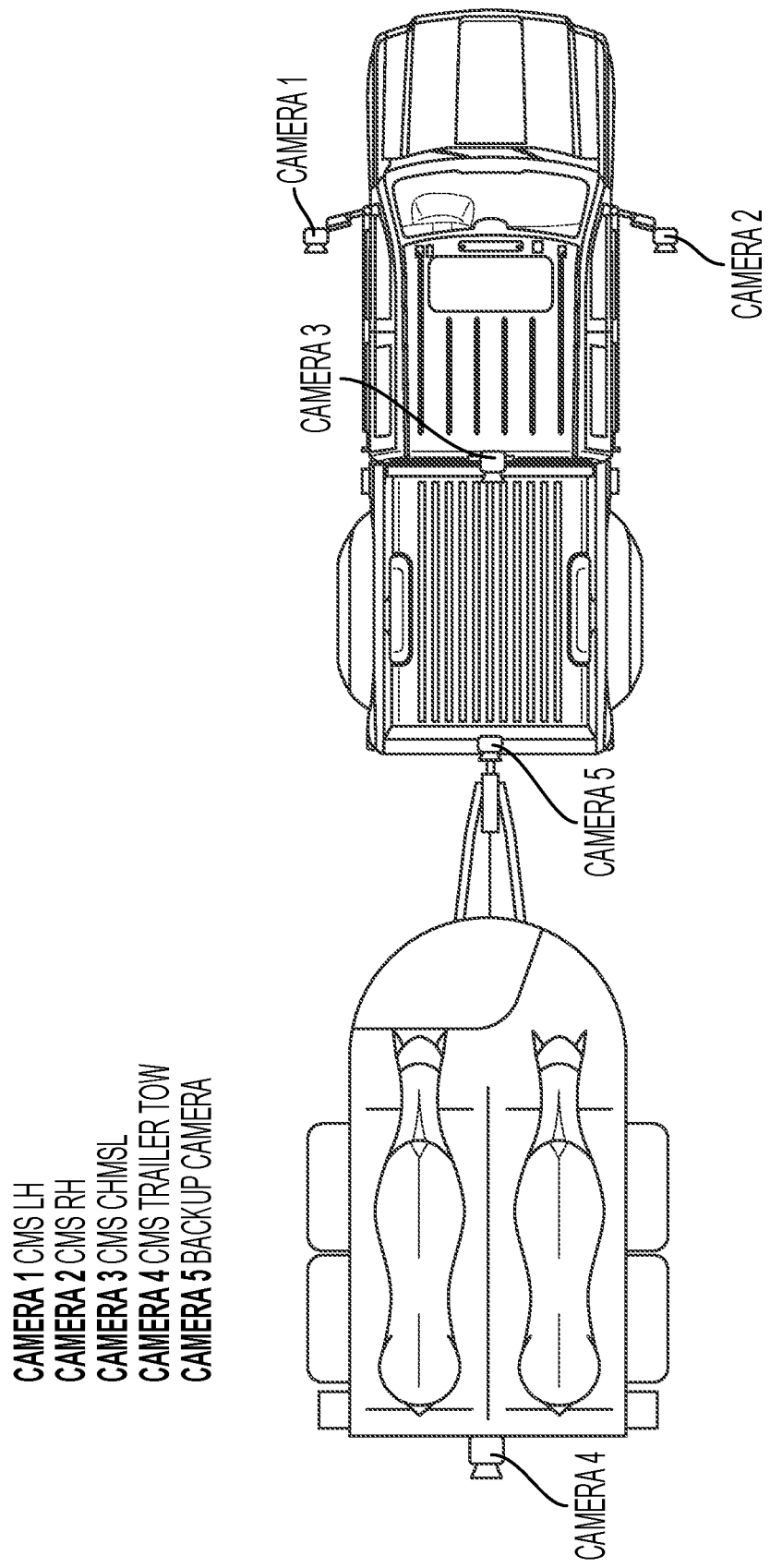
FIG. 27 is a plan view of a vehicle towing a trailer.

The interior rearview mirror assembly 20 provides a full mirror display via the display screen and backlight assembly disposed behind the mirror reflective element or EC cell (see FIG. 20). The mirror assembly may include a touch assembly (FIG. 21A), which may include customer branding. During assembling of the mirror assembly, the frame is placed at or on the EC cell (FIG. 21B), and the display screen and printed circuit board (PCB) is attached at the chassis (FIG. 21C). The bracket assembly or mounting assembly (including pivot joint and base or stay) is attached to the chassis (FIG. 21D), and the housing and rain sensor closeout is attached (FIG. 21E) to encase the PCB and display screen in the mirror head.

The cameras comprise digital cameras that capture image data and that are electrically connected to the remote ECU and/or mirror ECU via a coaxial cable connector and coaxial connector. FIGS. 22-26 show a suitable camera assembly for the rearward viewing and side cameras of the vision system. The back cover may be laser welded at the front cover so that the laser welding occurs away from the imager and PCB. The back cover may allow for lateral adjustment or floating relative to the front cover to align the connector. The camera may include a stamped EMC shield and a thermal pad for heat dissipation. The output of the camera may comprise a low voltage differential signaling (LVDS) digital signal, and the camera may be powered via power over coax.

During operation, the camera operates to capture frames of image data at 60 frames per second (or at 45 fps, 30 fps, 15 fps, or any suitable number of frames per second), and the capture rate may be adjusted to provide enhanced image capture in low lighting conditions and in high lighting conditions (e.g., the capture rate may be decreased in low lighting conditions and increased in high lighting conditions, such as responsive at least in part to an ambient light level at the vehicle, which may be determined by a separate ambient light sensor or via processing of image data captured by one of the exterior viewing cameras). The camera and/or system may optionally include hardware and/or software to reduce or mitigate visual flicker effects from LED signage or headlamps in the camera's field of view. For example, the LEDs that illuminate at least a portion of the field of view of the camera (such as the headlamps of the vehicle or an auxiliary LED, such as a near infrared light-emitting LED that is dedicated for illuminating the field of view of a respective camera or cameras when the camera is operating) may operate via pulse width modulation (PWM) in the range of 90 Hz to 400 Hz, and with a duty cycle greater than 10%.

Figure 28:
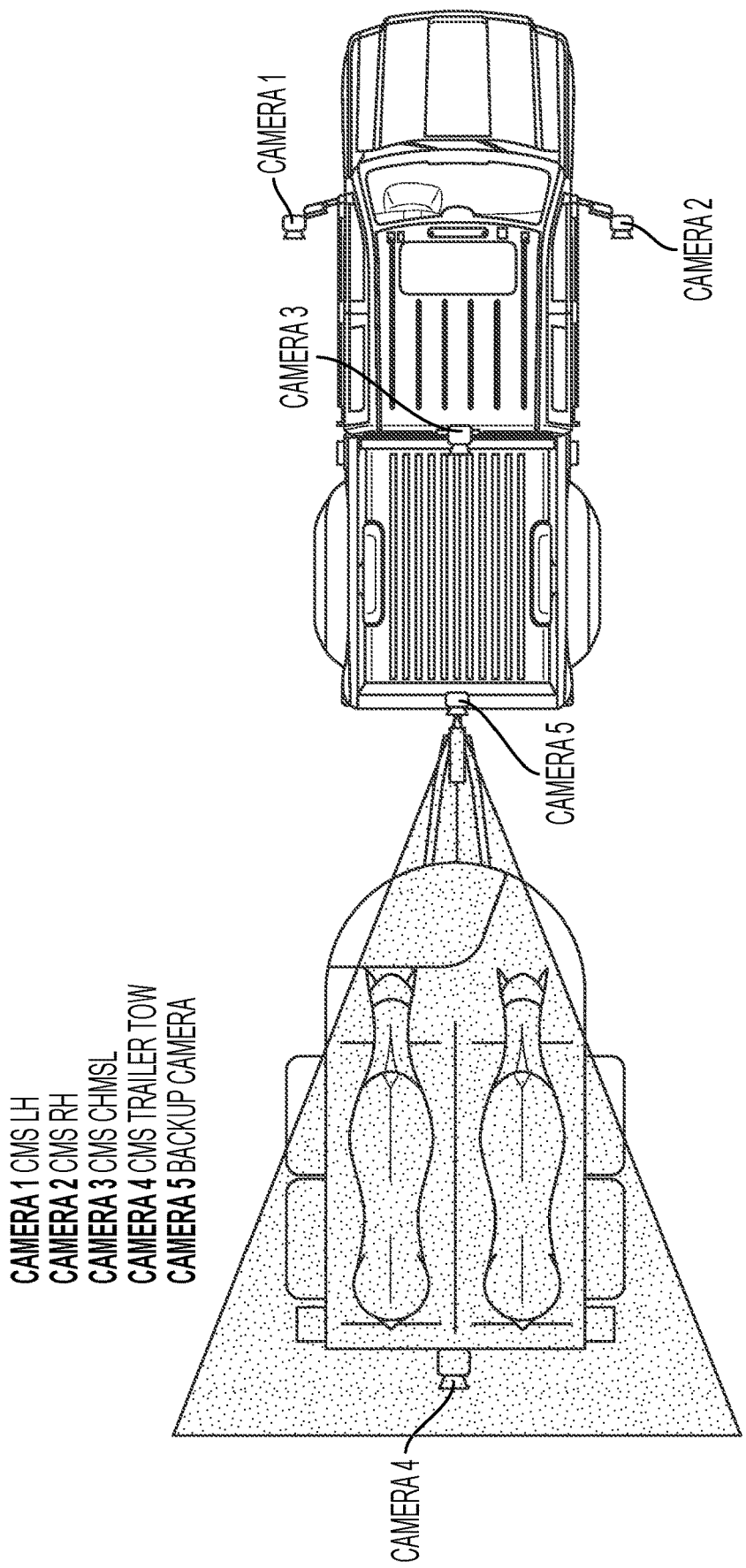
FIGS. 28-30 are views of the vehicle and trailer of FIG. 27, showing the trailer blocking the rearward view of the cameras.
Figure 29:
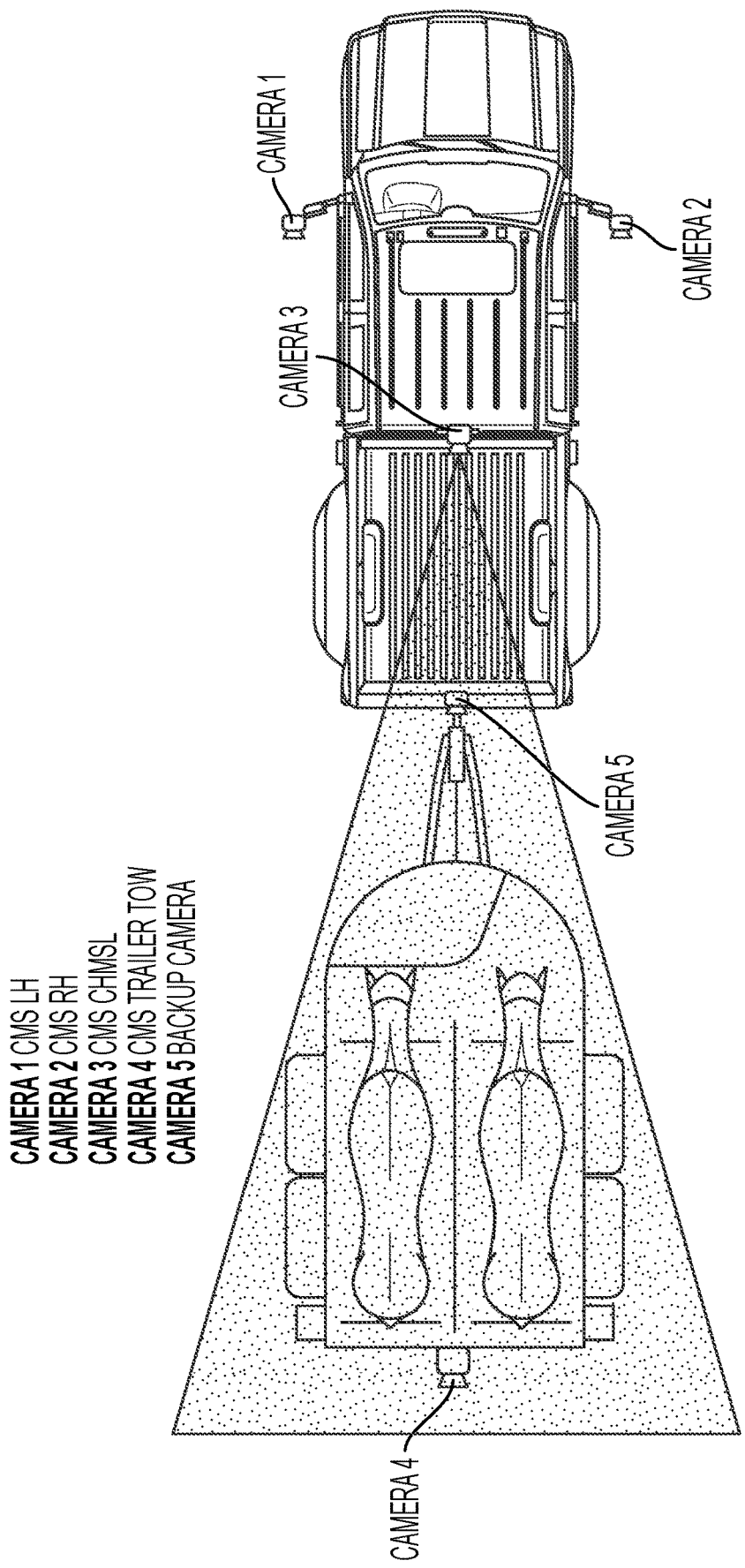
Figure 30:
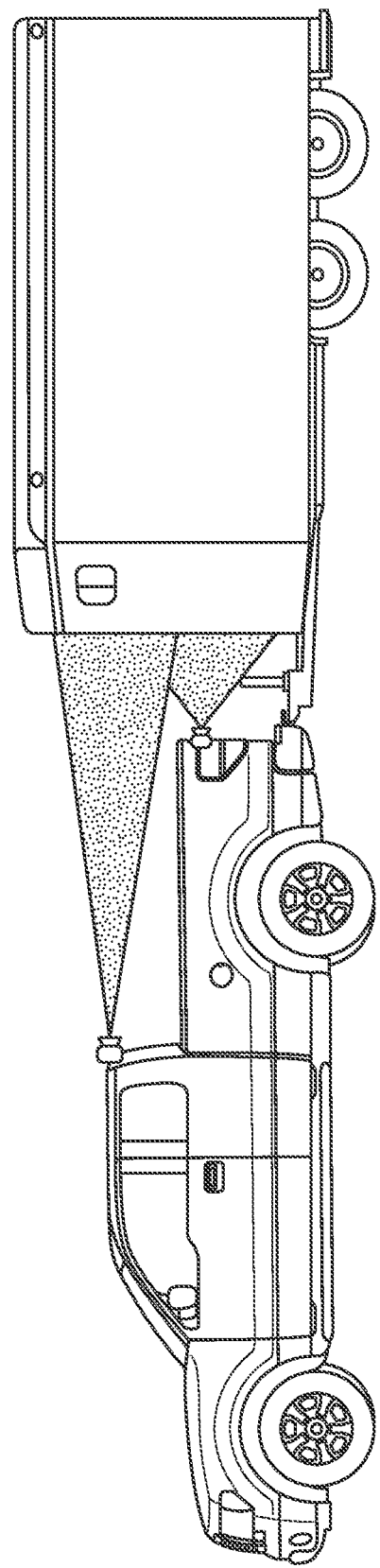

Optionally, the system may provide for dimming control of the electrochromic mirror reflective element of the interior mirror and of the electrochromic mirror reflective elements of the exterior mirrors via processing of image data captured by one or more of the cameras (such as by utilizing aspects of the vision systems described in U.S. Publication Nos. US-2019-0258131 and/or US-2019-0047475, which are hereby incorporated herein by reference in their entireties). For example, and with reference to FIGS. 27-31, the system may utilize a rearward sensing sensor at the mirror or the rearward viewing camera (at the CHMSL region) to determine glare light rearward of the vehicle when the vehicle is not towing a trailer. However, when the vehicle is towing a trailer that obstructs the rear window view, the trailer blocks the glare or rear sensing sensor at the interior mirror and blocks the rear backup camera view and blocks the CMS CHMSL camera view (see FIGS. 28-30). Thus, the presence of the trailer inhibits the ability for glare control for the exterior auto-dimming mirrors using the rearward sensing sensor and/or rearward viewing cameras of the vehicle. In such trailering situations, the system may utilize the CMS exterior side cameras for independently determining glare conditions for each respective exterior auto-dimming mirror. Thus, and as can be seen with reference to FIG. 31, the exterior CMS Cameras (Camera 1 and Camera 2) and the rearward viewing trailer camera (Camera 4) can be used to detect glare and determine the driver and passenger side auto-dimming mirror level of dimming independently. Thus, the ECU, responsive to processing of image data captured by the side rearward viewing CMS camera at a respective side of the vehicle, may control dimming of an exterior auto-dimming mirror reflective element of a side exterior rearview mirror assembly at that respective side of the vehicle, and the ECU, responsive to processing of image data captured by one or more of the side rearward viewing CMS cameras and the rearward viewing CMS camera, may also or otherwise control display intensity (via adjusting backlighting intensity) of the center console video display screen and the video mirror display screen (and optionally other interior vehicle lighting as well).

Figure 31:
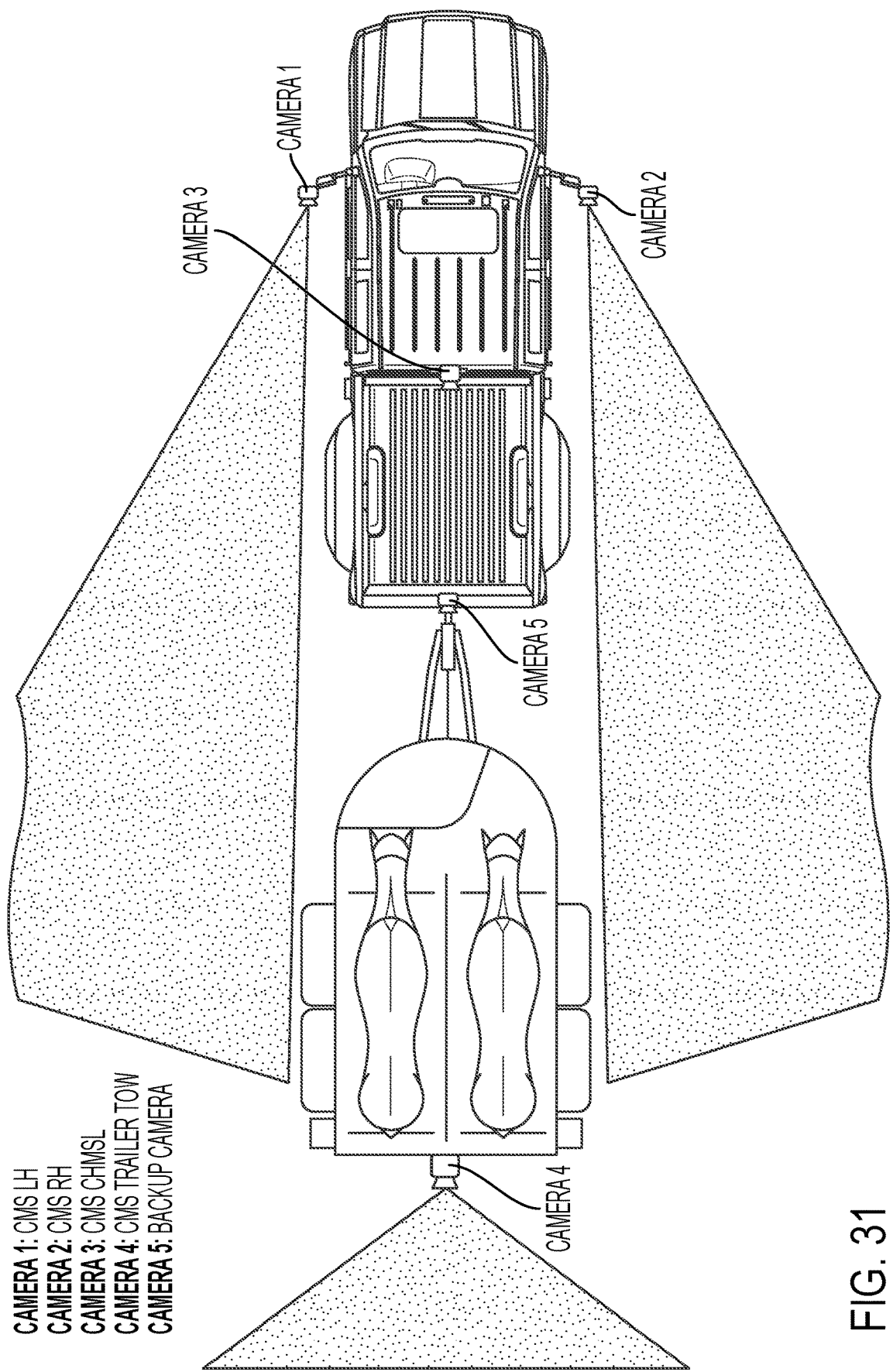
FIG. 31 is another plan view of the vehicle and trailer, showing use of the side cameras and the rearward viewing trailer-mounted camera to determine glare and/or to provide a CMS function.

As shown in FIG. 31, the side cameras are disposed at the respective exterior rearview mirror assemblies. The cameras may be disposed at an extendable and retractable mirror head that may extend/retract via telescoping arms or pivoting linkages or the like (such as by utilizing aspects of the mirror assemblies described in U.S. Pat. Nos. 5,483,385; 6,116,743; 6,213,609; 6,239,928; 6,276,808; 6,325,518; 6,394,616; 6,497,491; 7,267,449 and/or 9,796,334), whereby the mirror head is extendable outboard from the side of the vehicle by about six inches by a mechanical or electro-mechanical system.

Optionally, the side cameras may be disposed at the mirror base so that the cameras do not extend or move with the mirror head. The cameras may have a wide angle field of view so as to encompass a side region of the vehicle and the region sideward and rearward of the vehicle. The system may adjust the view of the camera (or adjust processing of the wide angle view to adjust the area that is displayed) based on whether or not a trailer is hitched to the vehicle and being towed by the vehicle.

Optionally, the system may determine (via processing of image data captured by the camera or cameras) whether or not a trailer is being towed by the vehicle and is encroaching the field of view of the camera. Responsive to determination that the trailer is being towed by the vehicle and is encroaching the field of view of the camera, the system can adjust the displayed images by adjusting the portion of the camera's view that is used for the video images (e.g., by shifting or cropping the image outward to accommodate the trailer's blockage of an inboard portion of the camera's view).

Optionally, the system may operate to determine presence of a trailer and to adjust processing of the camera's captured image data responsive to determination that the mirror head is extended or retracted (since such movement is indicative of a change in trailering status of the vehicle). For example, when the system determines presence of a trailer that encroaches the sideward and rearward field of view of the side camera, the system may adjust or index the used portion of the camera's field of view around 10 degrees (or such as 12 degrees or more or less) outboard from the vehicle. Optionally, the system may adjust or index the processing of the camera's captured image data responsive to extension and retraction of the mirror head or responsive to a user actuatable input that is actuatable by the driver of the vehicle. Thus, when a trailer is hitched to a vehicle and the mirrors are extended, the displayed video images (derived from image data captured by the side cameras) change or shift outward away from the side of the vehicle to provide the desired field of view sideward of the trailer.

Figure 32:
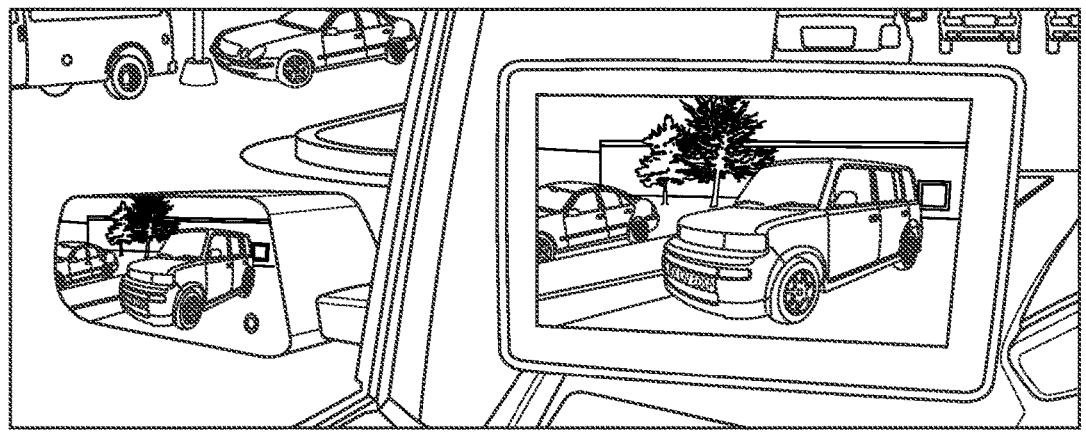
FIG. 32 is a perspective view of a CMS camera at an exterior rearview mirror, and showing a CMS display device at the A-pillar of the vehicle.
Figure 33:
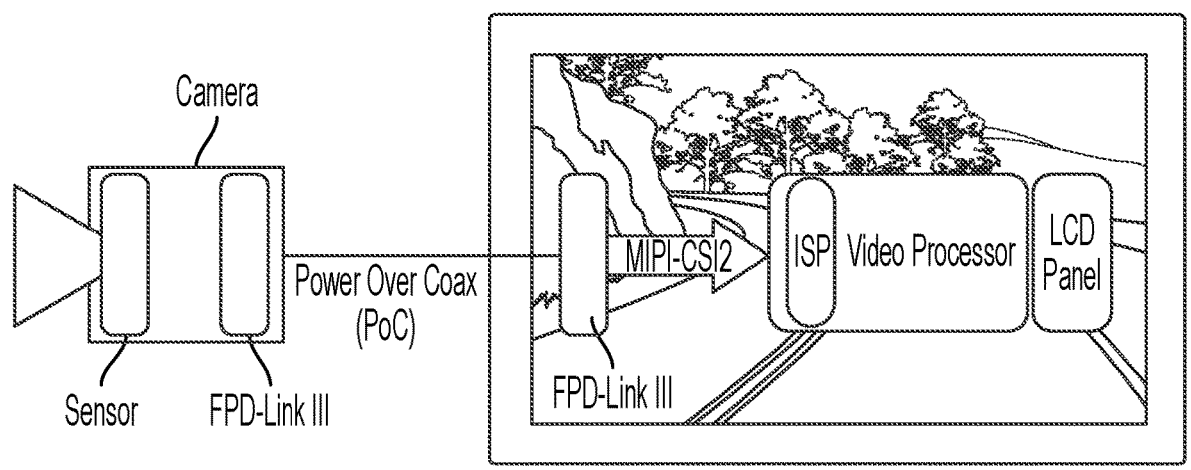
FIG. 33 is a block diagram of the camera and display device of FIG. 32.
Figure 34:
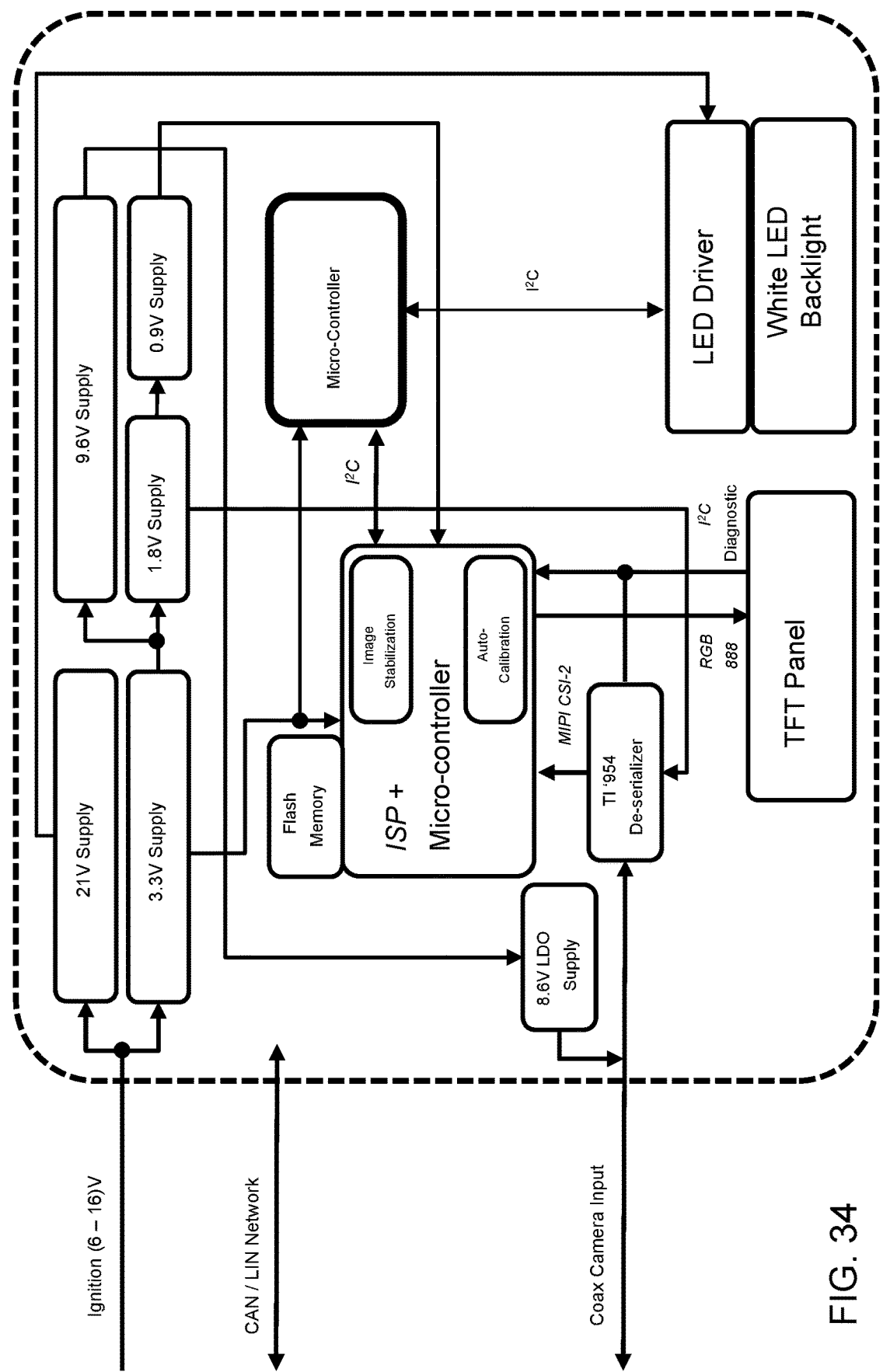
FIG. 34 is a block diagram of the display device.

As shown in FIG. 32, the camera may be disposed at the exterior rearview mirror assembly and the display may be disposed at the A-pillar of the vehicle. Optionally, the camera may replace the mirror assembly such that the camera is disposed at an arm that extends laterally outward from the side of the vehicle. Video images derived from video image data captured by the side mounted CMS camera are displayed at the video display screen disposed at the A-pillar near the camera or mirror assembly. As shown in FIGS. 33 and 34, the display device may include a video processor (comprising an image signal processor or ISP) that processes the video image data captured by the camera (and received at the display device via a coaxial cable (that may also provide power to the camera) and outputs an image signal to the LCD panel for display.

The outside mirror assembly thus integrates a camera with a regulatory compliant reflective mirror. Featuring a larger field of view, intuitive dynamic overlays and reduced drag, the system displays a live feed from the camera on the display screen integrated at the A-pillar. The small camera and mirror packaging reduces drag and provides increased forward visibility. The camera may provide a wider field of view (e.g., around 45 degrees or more) than the mirror reflective element (which may provide, for example, a field of view that extends horizontally about 12 degrees or thereabouts). The display may be customizable to user preferences. For example, the displayed images may include dynamic overlays to improve depth perception, such as red and yellow shading and/or a blind zone indicator. The exterior mirror assembly may include a turn signal indicator and may comprise a powerfold actuator. Optionally, the exterior mirror assembly may include a projection logo and/or ground illumination light module, and may also include a downward and sideward viewing camera (such as for a surround view vision system of the vehicle).

The CMS camera and display provides improved rear vision during low light conditions (such as by using a camera having an imager that is sensitive to infrared or near infrared light and/or such as by using an auxiliary light (e.g., a near infrared LED) that emits light within the field of view of the camera). The camera may provide dynamic digital aiming, and may be adjusted when the vehicle is reversing or changing lanes or cornering.

Figure 35:
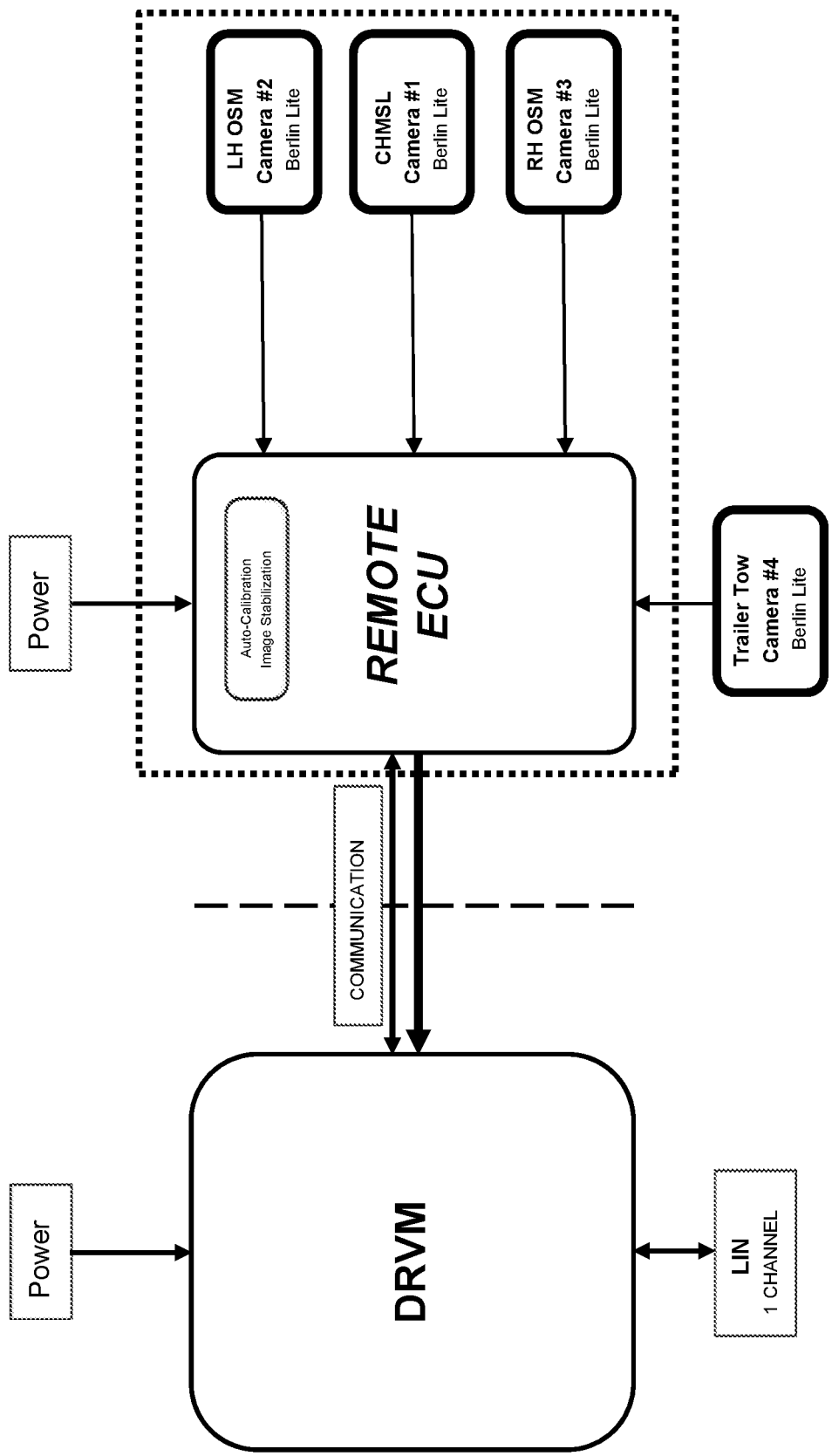
FIG. 35 is a block diagram of the camera monitoring system, using a remote ECU and a video display at an interior rearview mirror.
Figure 36:
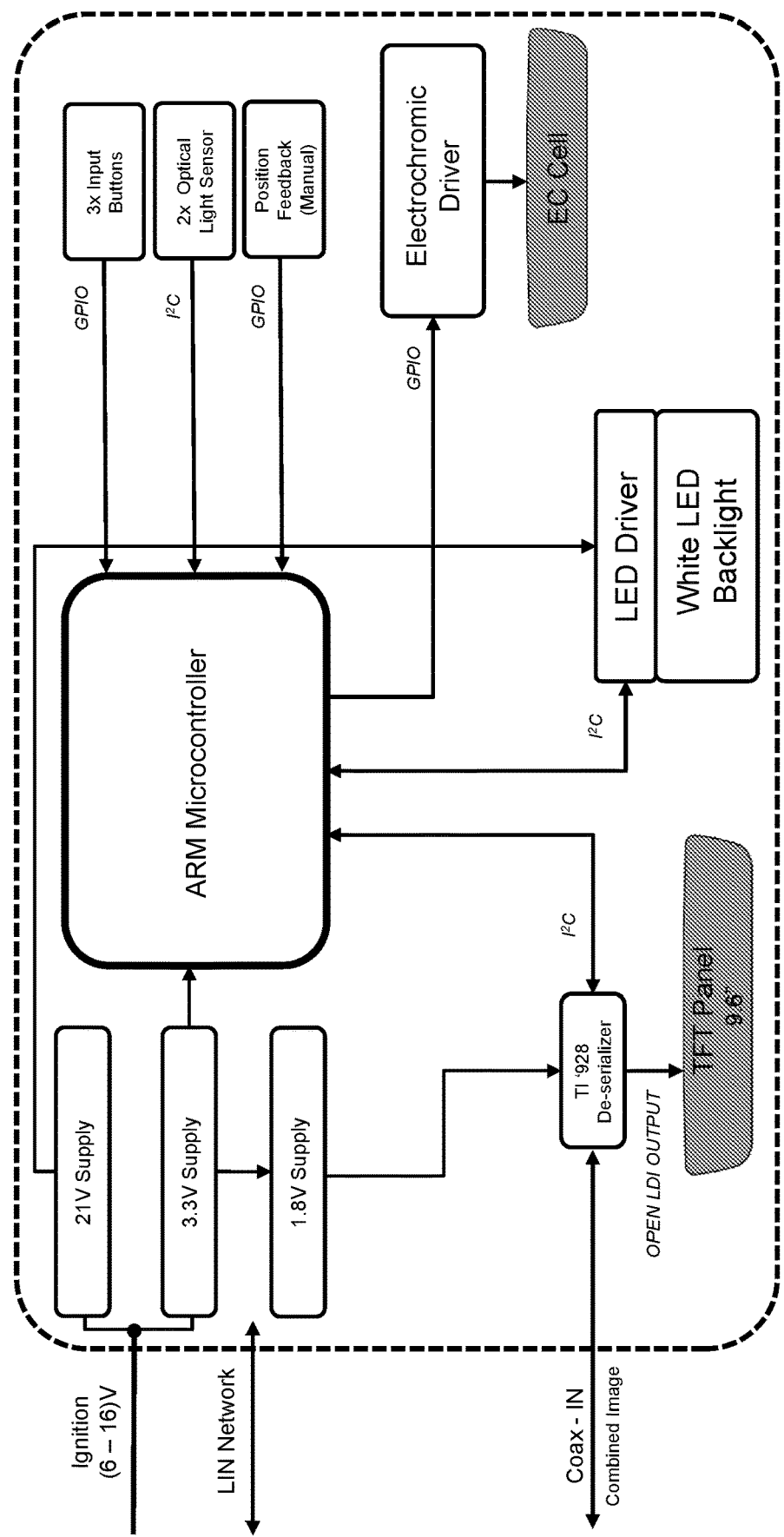
FIG. 36 is a block diagram of the interior rearview mirror.

As shown in FIG. 34, the interior display comprises a video processor comprising an ISP and microcontroller that receives image data from the camera via a coaxial cable, processes the image data, and outputs a display at the LCD panel. As shown in FIG. 35, the CMS cameras (and optionally a trailer tow camera, if applicable) provide image data to the ECU (located remote from the cameras and from the interior display), which processes the image data and outputs a display signal to the display device (such as a video display screen at the interior rearview mirror assembly). The display device may receive vehicle information or user inputs via a LIN communication bus or link. As shown in FIG. 36, the interior rearview mirror assembly receives the display signal via a coaxial cable and processes the signal for outputting to the display. The mirror assembly includes a microcontroller that outputs signals to an electrochromic driver of the EC cell and to an LED driver of the backlighting device of the display screen and to a de-serializer of the TFT display panel.

The microcontroller receives an input from a light sensor, and may control the EC driver and the LED backlighting responsive to a detected or determined ambient light level at the mirror assembly. The system may also control EC dimming of the exterior mirrors and control the display intensity of the respective display screens (e.g., at the respective A-pillars) responsive to processing of image data captured by the respective side CMS cameras. The system may also control the intensity of the interior mirror display responsive to processing of image data captured by one or both side CMS cameras or responsive to processing of image data captured by the rearward viewing CHMSL camera or responsive to processing of image data captured by the rear backup camera or responsive to processing of image data captured by the trailer camera. The data used for dimming control may be provided by one or more of the cameras (such as one or more of the CMS cameras) and/or may be provided via the CAN or LIN bus of the vehicle. Optionally, the system may operate to control the intensity of dash lights or other interior vehicle lighting and/or exterior vehicle lighting responsive to processing of image data captured by one or more of the CMS cameras (or surround vision cameras) of the vehicle. The data used for dimming control may be provided by one or more of the cameras (such as one or more of the CMS cameras) and/or may be provided via the CAN or LIN bus of the vehicle.

Figure 37:
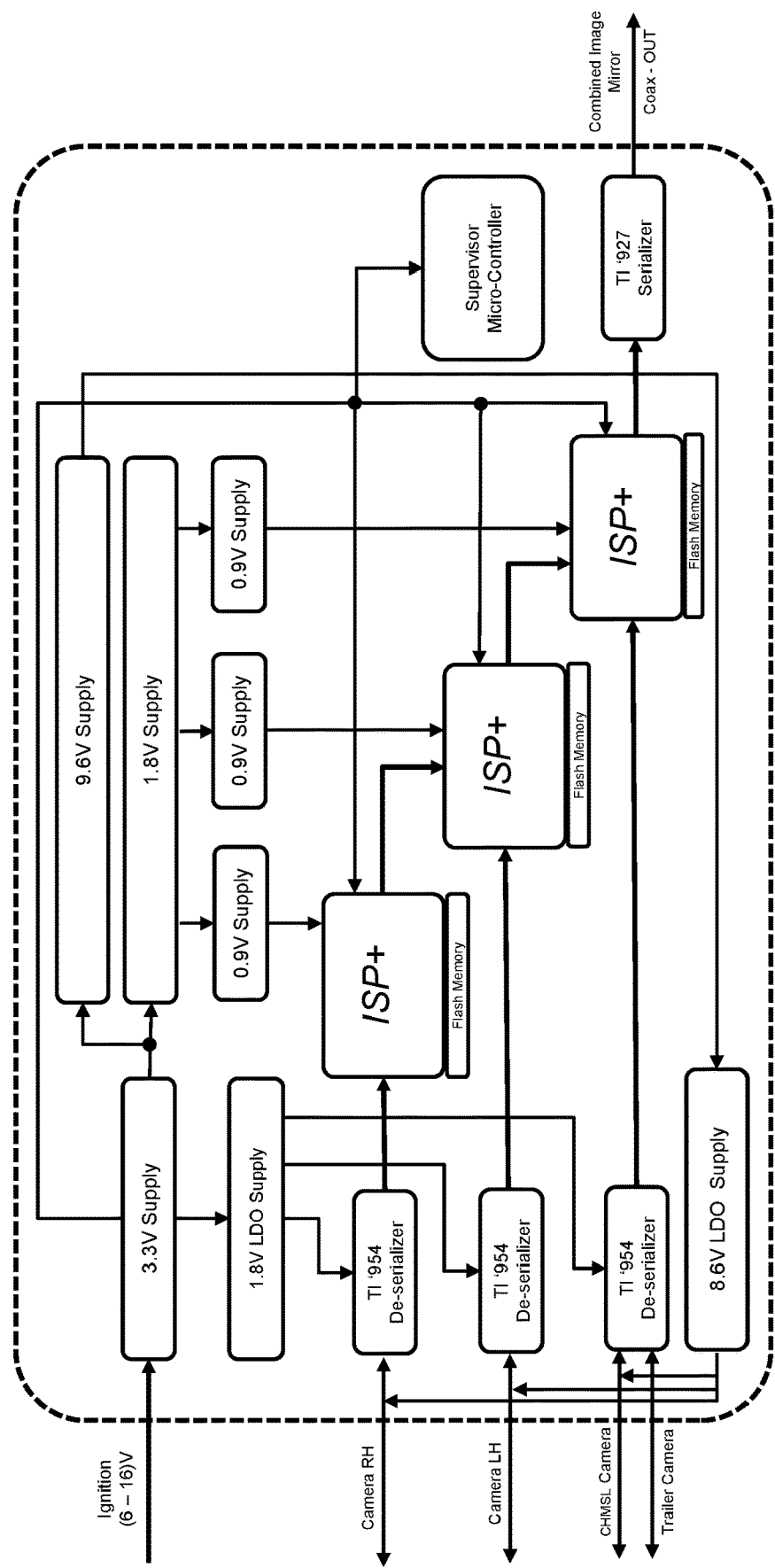
FIG. 37 is a block diagram of the remote ECU.

As shown in FIG. 37, the remote ECU may include multiple ISPs, with each one associated with one of the CMS cameras. The outputs of each ISP may be combined with other images at a downstream ISP, such that the CHMSL camera ISP outputs a combined image signal to the interior rearview mirror. The CHSML camera ISP may receive image data captured by the CHMSL camera or may receive image data captured by the trailer camera. For example, when a trailer is hitched to the vehicle and a trailer camera is communicating with the ECU, the system may automatically switch the input from the CHMSL camera to the trailer camera.

Optionally, the vehicle may be equipped with a blind zone detector (such as a radar sensor or the like that senses the region sideward of the vehicle that is not readily viewed by the driver of the vehicle). When another vehicle or object appears in the blind zone, the blind zone indicator (typically an icon or indicator at the exterior rearview mirror at that side of the vehicle) is actuated to alert the driver of the detected other vehicle at that side of the vehicle. The detection system outputs an electrical signal that is provided to the indicator and may also provide an electrical signal to the interior mirror display, such that, simultaneous with the indicator at the exterior mirror being actuated, the video display at the interior mirror is also actuated to provide an alert to the driver at the interior mirror as well. For example, detection of a vehicle in the blind zone at a particular side of the vehicle may result in video images (derived from image data captured by the side camera at that side of the vehicle) being displayed at the interior mirror (such as at a respective side region of the interior mirror) and/or may result in an icon or indicia (indicative of a detection, such as an icon similar to the icon of the blind zone indicator at the exterior mirror) appearing at interior mirror (such as at a respective side region of the interior mirror). Optionally, the indication at the interior mirror may be user selected (such as via a user actuatable input or switch or such as via a menu selection from a touch screen of the vehicle or the like) to provide the desired image and/or icon at the interior mirror and/or to provide no display or icon at the interior mirror, depending on the preferences of the driver of the vehicle. The blind zone indicating system may utilize aspects of the systems described in U.S. Pat. Nos. 9,041,806; 7,492,281 and/or 5,786,772, and/or U.S. Publication Nos. US-2018-0134217 and/or US-2014-0098230, which are hereby incorporated herein by reference in their entireties.

The cameras may comprise any suitable imaging sensor or camera, such as a pixelated imaging array or the like, such as a CMOS imaging array sensor, a CCD sensor or other sensors or the like, such as a camera or sensor of the types disclosed in commonly assigned, U.S. Pat. Nos. 7,965,336; 5,550,677; 5,760,962; 6,097,023 and 5,796,094, which are hereby incorporated herein by reference in their entireties. Optionally, the cameras may comprise a stereo imaging camera or the like, such as by utilizing aspects of the imaging systems described in U.S. Pat. Nos. 6,396,397 and/or 5,796,094, which are hereby incorporated herein by reference in their entireties. Optionally, the cameras may comprise an infrared or near infrared light sensitive camera and may be suitable for capturing images in low lighting conditions, and/or the camera may include or be associated with an illumination source (such as an infrared or near-infrared light emitting illumination source that, when actuated to emit infrared or near-infrared light at the side of the vehicle, enhances the camera's performance but is not visible or discernible to the driver of the vehicle), such as by utilizing aspects of the cameras described in U.S. Pat. Nos. 7,965,336; 5,550,677; 5,760,962; 6,097,023 and 5,796,094, which are hereby incorporated herein by reference in their entireties.

The sideward and rearward viewing cameras may be incorporated at the exterior rearview mirror assembly or elsewhere at the vehicle, such as at a side portion of the vehicle, and having a sideward and rearward field of view. Optionally, the camera may have a wide angle field of view at the side of the vehicle and/or may have an adjustable field of view and/or may capture images for use in other vision systems, such as for use in a top-down view or bird's-eye view vision system of the vehicle or a surround view vision system at the vehicle, such as by utilizing aspects of the vision systems described in U.S. Pat. Nos. 9,126,525; 9,041,806; 9,900,522; 9,900,522; 10,071,687 and/or 9,762,880, and/or U.S. Publication Nos. US-2015-0022664 and/or US-2012-0162427, which are hereby incorporated herein by reference in their entireties.

The mirror assembly may comprise any suitable construction, such as, for example, a mirror assembly with the reflective element being nested in the mirror casing and with a bezel portion that circumscribes a perimeter region of the front surface of the reflective element, or with the mirror casing having a curved or beveled perimeter edge around the reflective element and with no overlap onto the front surface of the reflective element (such as by utilizing aspects of the mirror assemblies described in U.S. Pat. Nos. 7,184,190; 7,274,501; 7,255,451; 7,289,037; 7,360,932; 7,626,749; 8,049,640; 8,277,059 and/or 8,529,108, which are hereby incorporated herein by reference in their entireties) or such as a mirror assembly having a rear substrate of an electro-optic or electrochromic reflective element nested in the mirror casing, and with the front substrate having curved or beveled perimeter edges, or such as a mirror assembly having a prismatic reflective element that is disposed at an outer perimeter edge of the mirror casing and with the prismatic substrate having curved or beveled perimeter edges, such as described in U.S. Pat. Nos. 8,508,831; 8,730,553; 9,598,016 and/or 9,346,403, and/or U.S. Publication Nos. US-2014-0313563 and/or US-2015-0097955, which are hereby incorporated herein by reference in their entireties (and with electrochromic and prismatic mirrors of such construction are commercially available from the assignee of this application under the trade name INFINITY™ mirror).

The mirror assembly may include user inputs or actuatable switches or touch sensors or the like for user/driver control of one or more features of the mirror assembly and/or display system. The user inputs or touch sensors may comprise any suitable sensors or inputs, and may utilize aspects of the inputs and sensors described in U.S. Pat. Nos. 9,827,913; 9,598,016; 9,346,403; 8,508,831; 8,730,553; 7,224,324; 7,253,723; 7,255,451 and/or 8,154,418, which are hereby incorporated herein by reference in their entireties.

Optionally, the display may utilize aspects of the displays of the types disclosed in U.S. Pat. Nos. 9,264,672; 9,041,806; 7,855,755; 7,777,611; 7,626,749; 7,581,859; 7,446,924; 7,446,650; 7,370,983; 7,338,177; 7,274,501; 7,255,451; 7,195,381; 7,184,190; 6,690,268; 6,329,925; 5,668,663; 5,530,240 and/or 5,724,187, and/or in U.S. Publication No. US-2006-0050018, which are all hereby incorporated herein by reference in their entireties. The display may be viewable through the reflective element when the display is activated to display information. The display element may be any type of display element, such as a vacuum fluorescent (VF) display element, a light emitting diode (LED) display element, such as an organic light emitting diode (OLED) or an inorganic light emitting diode, an electroluminescent (EL) display element, a liquid crystal display (LCD) element, a video screen display element or backlit thin film transistor (TFT) display element or the like, and may be operable to display various information (as discrete characters, icons or the like, or in a multi-pixel manner) to the driver of the vehicle, such as passenger side inflatable restraint (PSIR) information, tire pressure status, and/or the like.

Changes and modifications to the specifically described embodiments may be carried out without departing from the principles of the present invention, which is intended to be limited only by the scope of the appended claims as interpreted according to the principles of patent law.

The invention claimed is:

1. A vehicular vision system, the vehicular vision system comprising:
   an electronic control unit (ECU) disposed at a vehicle equipped with the vehicular vision system, wherein the ECU comprises electronic circuitry and associated software;
   a plurality of cameras disposed at the vehicle;
   wherein the plurality of cameras comprises (i) a rear backup camera, (ii) a left-side sideward viewing camera at a left side of the vehicle, (iii) a right-side sideward viewing camera at a right side of the vehicle and (iv) a rearward viewing camera having a different rearward view than the rear backup camera;
   wherein each camera of the plurality of cameras captures image data and provides captured image data to the ECU;
   wherein the electronic circuitry of the ECU comprises an image processor operable to process image data captured by the plurality of cameras;
   a video display screen disposed in the vehicle and viewable by a driver of the vehicle;
   wherein the ECU is operable to provide to the video display screen video images derived from image data captured by at least some cameras of the plurality of cameras, and wherein the video display screen is operable to display video images derived from video images provided by the ECU;
   a video mirror display screen disposed at an interior rearview mirror assembly of the vehicle and viewable by the driver of the vehicle;
   wherein the ECU is operable to provide to the video mirror display screen video images derived from image data captured by at least one camera of the plurality of cameras, and wherein the video mirror display screen is operable to display video images derived from video images provided by the ECU;
   wherein, when the vehicle is traveling forward at a speed below a threshold speed, the ECU, via processing of image data captured by at least the rearward viewing camera, generates rearward view video images and provides the rearward view video images to the video display screen; and
   wherein, when the vehicle is traveling forward at a speed at or above the threshold speed, the ECU, via processing of image data captured by at least the rearward viewing camera, generates rearward view video images and provides the rearward view video images to the video mirror display screen.

2. The vehicular vision system of claim 1, wherein the provided rearview video images are partial rearview images derived from a portion of the image data captured by the rearward viewing camera and processed at the ECU.

3. The vehicular vision system of claim 2, wherein the processed portion of the captured image data is adjustable.

4. The vehicular vision system of claim 3, wherein the processed portion of the captured image data is adjustable via a user input.

5. The vehicular vision system of claim 3, wherein the processed portion of the captured image data is adjusted based at least in part on an orientation of the video mirror display screen of the interior rearview mirror assembly.

6. The vehicular vision system of claim 1, wherein the ECU is remote from the video display screen and the video mirror display screen.

7. The vehicular vision system of claim 1, wherein the ECU is remote from the video mirror display screen, and wherein the video mirror display screen is electrically connected to the ECU via a coaxial cable, and wherein the ECU provides video images to the video mirror display screen via the coaxial cable.

8. The vehicular vision system of claim 1, wherein the ECU is remote from the video display screen, and wherein the video display screen is electrically connected to the ECU via a coaxial cable, and wherein the ECU provides video images to the video display screen via the coaxial cable.

9. The vehicular vision system of claim 1, wherein, when a trailer equipped with a rearward viewing trailer camera is hitched to the vehicle, the rearward viewing trailer camera has a field of view at least rearward of the trailer and captures image data, and wherein image data captured by the rearward viewing trailer camera is provided to the ECU.

10. The vehicular vision system of claim 9, wherein, with the trailer hitched to the vehicle, the video images provided by the ECU include video images derived from at least a portion of image data captured by the rearward viewing trailer camera.

11. The vehicular vision system of claim 10, wherein, during a reversing maneuver, the video images provided by the ECU are derived from a portion of image data captured by the rearward viewing trailer camera that corresponds to a lower region of the field of view of the rearward viewing trailer camera.

12. The vehicular vision system of claim 10, wherein, when the vehicle is traveling forward at a speed at or above the threshold speed, the rearward view video images provided by the ECU are derived from a portion of image data captured by the rearward viewing trailer camera that corresponds to an upper region of the field of view of the rearward viewing trailer camera.

13. The vehicular vision system of claim 9, wherein the ECU, via processing of image data captured by the rearward viewing trailer camera and the rearward viewing camera, generates see-through trailer video images and provides the see-through trailer video images to the video display screen or the video mirror display screen.

14. The vehicular vision system of claim 13, wherein, when the vehicle is traveling forward at a speed below the threshold speed, the ECU provides the see-through trailer video images to the video display screen.

15. The vehicular vision system of claim 14, wherein, when the vehicle is traveling forward at a speed at or above the threshold speed, the ECU provides the see-through trailer video images to the video mirror display screen of the interior rearview mirror assembly.

16. The vehicular vision system of claim 1, wherein, when the vehicle is traveling forward, the ECU, via processing of image data captured by at least the rearward viewing camera, is operable to provide the rearward view video images to the video display screen and to the video mirror display screen.

17. The vehicular vision system of claim 16, wherein the rearward view video images provided to the video display screen provide a different rearward view than the rearward view provided by the rearward view video images provided to the video mirror display screen.

18. The vehicular vision system of claim 1, wherein, during a reversing maneuver of the vehicle, the ECU, via processing of image data captured by at least (i) the rear backup camera, (ii) the left-side sideward viewing camera and (iii) the right-side sideward viewing camera, generates reverse-maneuver video images and provides the reverse-maneuver video images to the video display screen.

19. The vehicular vision system of claim 18, wherein, during the reversing maneuver of the vehicle, the ECU, via processing of image data captured by at least (i) the rear backup camera, (ii) the left-side sideward viewing camera and (iii) the right-side sideward viewing camera, generates other reverse-maneuver video images and provides the other reverse-maneuver video images to the video mirror display screen.

20. The vehicular vision system of claim 19, wherein the reverse-maneuver video images provided to the video display screen provide a different view than the view provided by the other reverse-maneuver video images provided to the video mirror display screen.

21. The vehicular vision system of claim 18, wherein the reverse-maneuver video images comprise top down surround view video images.

22. The vehicular vision system of claim 18, wherein the plurality of cameras comprises a front camera disposed at a front portion of the vehicle and viewing forward of the vehicle, and wherein the ECU generates the reverse-maneuver video images via processing of image data captured by (i) the rear backup camera, (ii) the left-side sideward viewing camera, (iii) the right-side sideward viewing camera and (iv) the front camera.

23. The vehicular vision system of claim 1, wherein the video display screen is disposed at a center console of the vehicle.

24. The vehicular vision system of claim 1, wherein the plurality of cameras comprises (i) a left-side rearward viewing camera disposed at the left side of the vehicle and having a different field of view than the left-side sideward viewing camera and (ii) a right-side rearward viewing camera disposed at the right side of the vehicle and having a different field of view than the right-side sideward viewing camera, and wherein, when the vehicle is traveling forward at a speed at or above the threshold speed, the ECU generates the rearward view video images via processing of at least portions of image data captured by (i) the rearward viewing camera, (ii) the left-side rearward viewing camera and (iii) the right-side rearward viewing camera.

25. A vehicular vision system, the vehicular vision system comprising:
an electronic control unit (ECU) disposed at a vehicle equipped with the vehicular vision system, wherein the ECU comprises electronic circuitry and associated software;
a plurality of cameras disposed at the vehicle;
wherein the plurality of cameras comprises (i) a rear backup camera, (ii) a left-side sideward viewing camera at a left side of the vehicle, (iii) a right-side sideward viewing camera at a right side of the vehicle and (iv) a rearward viewing camera having a different rearward view than the rear backup camera;
wherein each camera of the plurality of cameras captures image data and provides captured image data to the ECU;
wherein the electronic circuitry of the ECU comprises an image processor operable to process image data captured by the plurality of cameras;
a video display screen disposed in the vehicle and viewable by a driver of the vehicle;
wherein the video display screen is disposed at a center console of the vehicle;
wherein the ECU is operable to provide to the video display screen video images derived from image data captured by at least some cameras of the plurality of cameras, and wherein the video display screen is operable to display video images derived from video images provided by the ECU;
a video mirror display screen disposed at an interior rearview mirror assembly of the vehicle and viewable by the driver of the vehicle;
wherein the ECU is operable to provide to the video mirror display screen video images derived from image data captured by at least one camera of the plurality of cameras, and wherein the video mirror display screen is operable to display video images derived from video images provided by the ECU;
wherein, when the vehicle is traveling forward at a speed below a threshold speed, the ECU, via processing of image data captured by at least the rearward viewing camera, generates rearward view video images and provides the rearward view video images to the video display screen;
wherein, when the vehicle is traveling forward at a speed at or above the threshold speed, the ECU, via processing of image data captured by at least the rearward viewing camera, generates rearward view video images and provides the rearward view video images to the video mirror display screen; and
wherein, during a reversing maneuver of the vehicle, the ECU, via processing of image data captured by at least (i) the rear backup camera, (ii) the left-side sideward viewing camera and (iii) the right-side sideward viewing camera, generates reverse-maneuver video images and provides the reverse-maneuver video images to the video display screen.

26. The vehicular vision system of claim 25, wherein the ECU is remote from the video display screen and the video mirror display screen.

27. The vehicular vision system of claim 25, wherein the ECU is remote from the video mirror display screen, and wherein the video mirror display screen is electrically connected to the ECU via a coaxial cable, and wherein the ECU provides video images to the video mirror display screen via the coaxial cable.

28. The vehicular vision system of claim 25, wherein the ECU is remote from the video display screen, and wherein the video display screen is electrically connected to the ECU via a coaxial cable, and wherein the ECU provides video images to the video display screen via the coaxial cable.

29. The vehicular vision system of claim 25, wherein, when a trailer equipped with a rearward viewing trailer camera is hitched to the vehicle, the rearward viewing trailer camera has a field of view at least rearward of the trailer and captures image data, and wherein image data captured by the rearward viewing trailer camera is provided to the ECU.

30. The vehicular vision system of claim 29, wherein the ECU, via processing of image data captured by the rearward viewing trailer camera and the rearward viewing camera, generates see-through trailer video images and provides the see-through trailer video images to the video display screen or the video mirror display screen.

31. The vehicular vision system of claim 30, wherein, when the vehicle is traveling forward at a speed below the threshold speed, the ECU provides the see-through trailer video images to the video display screen, and wherein, when the vehicle is traveling forward at a speed at or above the threshold speed, the ECU provides the see-through trailer video images to the video mirror display screen of the interior rearview mirror assembly.

32. The vehicular vision system of claim 25, wherein, during the reversing maneuver of the vehicle, the ECU, via processing of image data captured by at least (i) the rear backup camera, (ii) the left-side sideward viewing camera and (iii) the right-side sideward viewing camera, generates other reverse-maneuver video images and provides the other reverse-maneuver video images to the video mirror display screen.

33. The vehicular vision system of claim 25, wherein the reverse-maneuver video images comprise top down surround view video images.

34. The vehicular vision system of claim 25, wherein the plurality of cameras comprises a front camera disposed at a front portion of the vehicle and viewing forward of the vehicle, and wherein the ECU generates the reverse-maneuver video images via processing of image data captured by (i) the rear backup camera, (ii) the left-side sideward viewing camera, (iii) the right-side sideward viewing camera and (iv) the front camera.

35. The vehicular vision system of claim 25, wherein the plurality of cameras comprises (i) a left-side rearward viewing camera disposed at the left side of the vehicle and having a different field of view than the left-side sideward viewing camera and (ii) a right-side rearward viewing camera disposed at the right side of the vehicle and having a different field of view than the right-side sideward viewing camera, and wherein, when the vehicle is traveling forward at a speed at or above the threshold speed, the ECU generates the rearward view video images via processing of at least portions of image data captured by (i) the rearward viewing camera, (ii) the left-side rearward viewing camera and (iii) the right-side rearward viewing camera.

36. A vehicular vision system, the vehicular vision system comprising:
an electronic control unit (ECU) disposed at a vehicle equipped with the vehicular vision system, wherein the ECU comprises electronic circuitry and associated software;
a plurality of cameras disposed at the vehicle;
wherein the plurality of cameras comprises (i) a rear backup camera, (ii) a left-side sideward viewing camera at a left side of the vehicle, (iii) a right-side sideward viewing camera at a right side of the vehicle and (iv) a rearward viewing camera having a different rearward view than the rear backup camera;
wherein each camera of the plurality of cameras captures image data and provides captured image data to the ECU;
wherein the electronic circuitry of the ECU comprises an image processor operable to process image data captured by the plurality of cameras;
a video display screen disposed in the vehicle and viewable by a driver of the vehicle;
wherein the video display screen is disposed at a center console of the vehicle;
wherein the ECU is operable to provide to the video display screen video images derived from image data captured by at least some cameras of the plurality of cameras, and wherein the video display screen is operable to display video images derived from video images provided by the ECU;
wherein the ECU is remote from the video display screen, and wherein the video display screen is electrically connected to the ECU via a first coaxial cable, and wherein the ECU provides video images to the video display screen via the first coaxial cable;
a video mirror display screen disposed at an interior rearview mirror assembly of the vehicle and viewable by the driver of the vehicle;
wherein the ECU is operable to provide to the video mirror display screen video images derived from image data captured by at least one camera of the plurality of cameras, and wherein the video mirror display screen is operable to display video images derived from video images provided by the ECU;
wherein, when the vehicle is traveling forward at a speed below a threshold speed, the ECU, via processing of image data captured by at least the rearward viewing camera, generates rearward view video images and provides the rearward view video images to the video display screen; and
wherein, when the vehicle is traveling forward at a speed at or above the threshold speed, the ECU, via processing of image data captured by at least the rearward viewing camera, generates rearward view video images and provides the rearward view video images to the video mirror display screen.

37. The vehicular vision system of claim 36, wherein the ECU is remote from the video mirror display screen, and wherein the video mirror display screen is electrically connected to the ECU via a second coaxial cable, and wherein the ECU provides video images to the video mirror display screen via the second coaxial cable.

38. The vehicular vision system of claim 36, wherein, when a trailer equipped with a rearward viewing trailer camera is hitched to the vehicle, the rearward viewing trailer camera has a field of view at least rearward of the trailer and captures image data, and wherein image data captured by the rearward viewing trailer camera is provided to the ECU.

39. The vehicular vision system of claim 38, wherein the ECU, via processing of image data captured by the rearward viewing trailer camera and the rearward viewing camera, generates see-through trailer video images and provides the see-through trailer video images to the video display screen or the video mirror display screen.

40. The vehicular vision system of claim 39, wherein, when the vehicle is traveling forward at a speed below the threshold speed, the ECU provides the see-through trailer video images to the video display screen, and wherein, when the vehicle is traveling forward at a speed at or above the threshold speed, the ECU provides the see-through trailer video images to the video mirror display screen of the interior rearview mirror assembly.

41. The vehicular vision system of claim 36, wherein the plurality of cameras comprises (i) a left-side rearward viewing camera disposed at the left side of the vehicle and having a different field of view than the left-side sideward viewing camera and (ii) a right-side rearward viewing camera disposed at the right side of the vehicle and having a different field of view than the right-side sideward viewing camera, and wherein, when the vehicle is traveling forward at a speed at or above the threshold speed, the ECU generates the rearward view video images via processing of at least portions of image data captured by (i) the rearward viewing camera, (ii) the left-side rearward viewing camera and (iii) the right-side rearward viewing camera.

\* \* \* \* \*